United States Patent
Tiwari et al.

(10) Patent No.: US 10,016,515 B2
(45) Date of Patent: Jul. 10, 2018

(54) DMA, A BIS-BENZIMIDAZOLE, CONFERS RADIOPROTECTION TO THE INTESTINE VIA AKT/NFκB DUAL PATHWAY ACTIVATION

(71) Applicants: Vibha Tandon, New Delhi (IN); Jawaharlal Nehru University, New Delhi (IN)

(72) Inventors: Vinod Tiwari, Delhi (IN); Vibha Tandon, New Delhi (IN)

(73) Assignees: JAWAHARLAL NEHRU UNIVERSITY, New Delhi (IN); Vibha Tandon, New Delhi (IN)

(*) Notice: Subject to any disclaimer, the term of this patent is extended or adjusted under 35 U.S.C. 154(b) by 0 days.

(21) Appl. No.: 15/220,631

(22) Filed: Jul. 27, 2016

(65) Prior Publication Data
US 2018/0028689 A1   Feb. 1, 2018

(51) Int. Cl.
  *A61K 49/00* (2006.01)
  *C07D 403/04* (2006.01)
  *A61N 5/10* (2006.01)
  *A61K 31/496* (2006.01)

(52) U.S. Cl.
  CPC ........ *A61K 49/0008* (2013.01); *A61K 31/496* (2013.01); *A61N 5/10* (2013.01); *C07D 403/04* (2013.01)

(58) Field of Classification Search
  CPC ........ A61K 49/00; A61K 31/496; A61N 5/10; C07D 403/04
  See application file for complete search history.

(56) References Cited

FOREIGN PATENT DOCUMENTS

IN  241650   7/2010

OTHER PUBLICATIONS

Kaur et al., PLos One (2012), 7 (6), e39426.*
Begg et al., 2011, "Strategies to improve radiotherapy with targeted drugs," Nature Reviews Cancer, 11:239-253.
Brizel et al., 2000, "Phase III randomized trial of amifostine as a radioprotector in head and neck cancer," Journal of Clinical Oncology, 18:3339-3345.
Burdelya et al., 2008, "An agonist of toll-like receptor 5 has radioprotective activity in mouse and primate models," Science, 320:226-230.
Kalpana et al., 2011, "Evaluating the radioprotective effect of hesperidin in the liver of Swiss albino mice," European Journal of Pharmacology 658:206-212.
Kamran et al., 2016, "Radioprotective Agents: Strategies and Translational Advances," Medicinal research reviews, 00(0):1-33.
Kaur et al., 2012, "DMA, a bisbenzimidazole, offers radioprotection by promoting NFκB transactivation through NIK/IKK in human glioma cells," PloS one 7:e39426.
Nair et al., 2001, "Radioprotectors in radiotherapy," Journal of Radiation Research, 42:21-37.
Nimesh et al., 2015, "Preclinical Evaluation of DMA, a Bisbenzimidazole, as Radioprotector: Toxicity, Pharmacokinetics, and Biodistribution Studies in Balb/c Mice," Molecular Pharmacology, 88:768-778.
Prabhakar et al., 2007, "Antioxidant and radioprotective effect of the active fraction of *Pilea microphylla* (L.) ethanolic extract," Chemico-Biological Interactions, 165:22-32.
Ranjan et al., 2013, "3,4-Dimethoxyphenyl bis-benzimidazole derivative, mitigates radiation-induced DNA damage," Radiation Research, 179:647-662.
Singh and Tandon, 2011, "Synthesis and biological activity of novel inhibitors of topoisomerase I: 2-aryl-substituted 2-bis-1H-benzimidazoles," European Journal of Medicinal Chemistry, 46:659-669.
Singh et al., 1998, "Radioprotective effects of DNA ligands Hoechst-33342 and 33258 in whole body irradiated mice," Indian Journal of Experimental Biology 36:375-384.
Tawar et al., 2007, "Nuclear condensation and free radical scavenging: a dual mechanism of bisbenzimidazoles to modulate radiation damage to DNA," Molecular and Cellular Biochemistry, 305:221-233.
Tawar et al., 2003, "Influence of phenyl ring disubstitution on bisbenzimidazole and terbenzimidazole cytotoxicity: synthesis and biological evaluation as radioprotectors," Journal of Medicinal Chemistry 46:3785-3792.
Wang et al., 2013, "Synthesis, radioprotective activity and pharmacokinetics characteristic of a new stable nitronyl nitroxyl radical-NIT2011," Biochimie 95:1574-1581.
Young, S.D., and R.P. Hill, 1989, "Radiation sensitivity of tumour cells stained in vitro or in vivo with the bisbenzimide fluorochrome Hoechst 33342," British Journal of Cancer 60:715-721.

* cited by examiner

Primary Examiner — Alexander R Pagano
Assistant Examiner — Ebenezer O Sackey
(74) Attorney, Agent, or Firm — Biospark Intellectual Property Law

(57) ABSTRACT

The present invention relates to dual activation of Akt/NFκB pathway by DMA (5-(4-methylpiperazin-1-yl)-2-[2'-(3,4-dimethoxyphenyl)-5'-benzimidazolyl]benzimidazole) to render radioprotection both in mammalian cells and in Balb/c mice. Further it selectively protects normal cells overs tumor tissues against lethal total body irradiation (TBI) and there was no activation of Akt/NFκB pathway by DMA in response to radiation in tumor tissues. A single dose of DMA before TBI protect mice from GI and HP acute radiation syndrome (ARS) and offered radioprotection through oral, i.v., i.p., and s.c route of administration. The half life of DMA in plasma is 3.5 h at oral dose and 90% clearance was observed in 16 h. DMA accumulates in high concentration in intestine, liver, kidney and spleen tissues, justifying the observed radioprotection to normal tissue even at single dose. This data provide molecular rationale that DMA is selective radioprotector to normal tissue and has the potential to improve clinical outcome of radiotherapy, valuable as adjuvants in cancer therapy and management of radiation emergencies.

16 Claims, 9 Drawing Sheets

DMA, A BIS-BENZIMIDAZOLE, CONFERS RADIOPROTECTION TO THE INTESTINE VIA AKT/NFκB DUAL PATHWAY ACTIVATION

FIELD OF THE INVENTION

The present invention relates to dual activation of Akt/NFκB pathway by DMA (5-(4-methylpiperazin-1-yl)-2-[2'-(3,4-dimethoxyphenyl)-5'-benzimidazolyl]benzimidazole) to render radioprotection both in mammalian cells and in Balb/c mice. Further it selectively protects normal cells overs tumor tissues against lethal total body irradiation (TBI) and there was no activation of Akt/NFκB pathway by DMA in response to radiation in tumor tissues. It relates to a method of radioprotection in both mammalian cells and normal tissues in a melanoma and ehrlich ascites tumor bearing mice comprising administering an effective amount of (5-(4-methylpiperazin-1-yl)-2-[2'-(3,4-dimethoxyphenyl)-5'-benzimidazolyl]benzimidazole (DMA) before receiving radiation therapy.

BACKGROUND OF THE INVENTION

Radiotherapy is utilized by 80% patients as a part of cancer treatment (Nair et al., 2001). Ionizing radiation (IR) causes generation of reactive oxygen species (ROS) and has deleterious effects on cells (Kalpana et al., 2011). Radiation attenuates the endogenous antioxidant enzymes which maintain redox balance and normal biochemical processes (Prabhakar et al., 2007). The two complementary strategies with drugs to enhance therapeutic index of radiotherapy are to increase radiation-induced cell death in tumor and reduce damage in surrounding normal tissues. This can be achieved by modulation of DNA repair, cell cycle, signal transduction pathway, normal tissue damage and/or increase in radio-sensitization of tumor (Begg et al., 2011). Radioprotectors protect normal cell from radiation induced damage. Mechanisms for radioprotection includes inhibition of free radicals generation or acceleration of scavenging free radicals, enhancement of DNA and membrane repair, reconstruction of HP function and stimulation of immune cell activity (Wang et al., 2013). Amifostine (WR2721) is a clinically approved radioprotector in cancer treatment for reducing side effects in patients undergoing radiotherapy (Brizel et al., 2000). Other known radioprotectors are methylproamine, PrC-210 and ON01210/Ex-RAD® (Kamran et al., 2016). These radioprotectors are associated with limitation by route of administration and related toxicity. CBLB502 had shown an excellent selective radioprotection to healthy cells over cancerous cells through constitutive activation of NFκB pathway as Toll-Like receptor 5 agonist (Burdelya et al., 2008).

The DNA ligands such as bisbenzimidazoles Hoechst 33342 and Hoechst 33258, form strong and non-covalent linkages, with the adenine and thymine rich regions in the minor groove of DNA, significantly altering the chromatin structure. Administration of these compounds prior to irradiation afford protection against the formation of primary lesions in the aqueous solutions of DNA as well as in the intact cell nucleus. These DNA ligands have also been observed to reduce the radiation induced cytogenetic damage and cell death in cell cultures, as well as in whole body irradiated animals (Singh et al., 1998; Young and Hill, 1989). However, post-irradiation treatment of cells with these ligands has been observed to enhance cell death in vitro (Singh et al., 1998). Free radical scavenging and quenching of DNA radicals appear to be the mechanisms responsible for protection by Hoechst compounds administered prior to irradiation, but its role in enhancing the radiation-induced cell death when administered after irradiation is not clearly understood.

The limitations of these minor groove binding ligands as being mutagenic, clatogenic and cytotoxic because of the DNA lesions caused on account of topoisomerase I inhibition, gene expression alteration and repair inhibition prevent them from being used in humans. Therefore, the development of DNA binding ligands (Minor Groove Binding Ligands particularly) that afford radioprotective effect without significant mutagenicity and cytotoxic effects can play a significant role in biological radiation protection. Although numbers of radioprotectors are developed, there is only one approved radioprotector. Therefore there is necessity for alternative, nontoxic and effective radioprotector with multiple modes of actions for better radioprotection.

Our earlier in vitro work proved DMA as non-toxic free radical scavenging radioprotector (Kaur et al., 2012; Singh and Tandon, 2011; Tawar et al., 2007; Tawar et al., 2003). It did not show toxicity in vivo at maximum tolerated dose (MTD) of 2000 mg/kg. DMA was effective to deliver radioprotective effect at $\frac{1}{7}$ dose of its MTD at 8Gy TBI (Nimesh et al., 2015). DMA induces NIK mediated NFκB activation and modulates number of key regulatory pathways including effector proteins (TP53, HSP70, SET, NPM and UBC) to overcome radiation induce damage (Kaur et al., 2012; Ranjan et al., 2013). In the present invention investigation has been carried out for the molecular mechanism to decipher the ability of DMA to protect normal and tumor bearing Balb/c mice against radiation-induced HP/GI injury, regulation of cellular antioxidant level, and modulatory effect on mRNA expression. The inventors showed that single 200 mg/kg oral and 50 mg/kg intravenous (i.v.) DMA dose augments 80 and 100% survival at 8Gy respectively through Akt/NFκB pathway, maintenance of antioxidant enzymes, improving HP & GI conditions and modulation of genes in TBI in vivo.

SUMMARY OF THE INVENTION

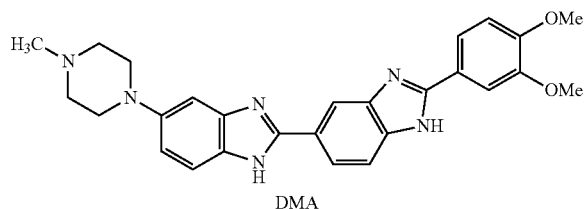

DMA

The present invention relates to dual activation of Akt/NFκB pathway by DMA (5-(4-methylpiperazin-1-yl)-2-[2'-(3,4-dimethoxyphenyl)-5'-benzimidazolyl]benzimidazole) to render radioprotection both in mammalian cells and in Balb/c mice. Further it selectively protects normal cells overs tumor tissues against lethal total body irradiation (TBI) and there was no activation of Akt/NFκB pathway by DMA in response to radiation in tumor tissues. It relates to a method of radioprotection in both mammalian cells and normal tissues in a melanoma and ehrlich ascites tumor bearing mice comprising administering an effective amount of (5-(4-methylpiperazin-1-yl)-2-[2'-(3,4-dimethoxyphenyl)-5'-benzimidazolyl]benzimidazole (DMA) before receiving radiation therapy.

Maximum DNA bound intensity of DMA (uptake of DMA) reached in 2 h in HEK293 cell. This intensity reduced gradually in next 72 h. Growth kinetics data suggested higher proliferation of MRC-5 cells as compared to A549 cells in presence of 50 μM DMA prior to 6 Gy radiation. DMA was cytotoxic to MRC5 cells at 92.51 μM at 24 h and its cytotoxicity could not be achieved in A549 till 72 h up to 100 μM concentration. The lower or no toxicity in A549 may be related to activation of efflux pump in this cell. There was no observable $IC_{50}$ in HEK293, MRC5 and A549 cell lines when short term treatment of DMA at 509 μM for 2 h was given. DMA exhibited better radioprotection in normal cells as compared to cancerous cells. DRF was highest 1.44 in HEK293 cells which are near normal cells and 1.067 in U87 cells. DRF was 1.1 in MRC5 as compared to A549 where it was 1.38.

DMA was effective radioprotector in vivo which exhibited protection against lethal TBI in Balb/c mice at various single DMA doses by oral (p.o.), intravenous (i.v.), intraperitoneal (i.p.) and subcutaneous (s.c.) with dose reduction factor (DRF) of 1.28. It has radioprotective effect in nude mice as well.

DMA does not exhibit radioprotection in tumor against TBI in tumor bearing mice (TBM). It demonstrated protection of normal tissues against radiation induced damage in TBM. Hence there was increased survival of TBM as compared to irradiated TBM.

DMA amileorate radiation induced hematopoietic (HP) and gastrointestinal (GI) system damage. It also recovered HP & GI damage in irradiated TBM. DMA pretreatment to radiation showed increased cell proliferation as compared to irradiated mice only. DMA also regulates radiation induced redox balance in murine.

DMA showed rapid clearance from plasma when delivered by both oral and i.v. routes of administration. It has preferential accumulation in small intestine.

DMA regulates cell proliferation and apoptosis related genes in intestine of irradiated Balb/c mice. It donot alter cell cycle and regulates Akt/NFκB signalling transduction pathway to render radioprotection in normal mice. Knockdown of Akt and NFκB p65 demonstrated no radioprotection by DMA and thus confirming the Akt/NFκB axis as modulatory pathway for radioprotection.

DMA donot activates Akt/NFκB pathway in tumor tissues of TBM against radiation and thus do not offer radioprotection in tumor tissues.

DETAILED DESCRIPTION OF THE INVENTION

The present invention relates to dual activation of Akt/ NFκB pathway by DMA (5-(4-methylpiperazin-1-yl)-2-[2'-(3,4-dimethoxyphenyl)-5'-benzimidazolyl]benzimidazole) to render radioprotection both in mammalian cells and in Balb/c mice. Further it selectively protects normal cells overs tumor tissues against lethal total body irradiation (TBI) and there was no activation of Akt/NFκB pathway by DMA in response to radiation in tumor tissues. It relates to a method of radioprotection in both mammalian cells and normal tissues in a melanoma and ehrlich ascites tumor bearing mice comprising administering an effective amount of (5-(4-methylpiperazin-1-yl)-2-[2'-(3,4-dimethoxyphenyl)-5'-benzimidazolyl]benzimidazole (DMA) before receiving radiation therapy.

The present invention investigated the molecular mechanism to decipher the ability of DMA to protect normal and normal tissues of tumor bearing Balb/c mice against radiation-induced HP/GI injury, regulation of cellular antioxidant level, and modulatory effect on mRNA expression.

In one of the embodiments the inventors showed that single 200 mg/kg oral and 50 mg/kg intravenous (i.v.) DMA dose augments 80 and 100% survival at 8Gy respectively through Akt/NFκB pathway, maintenance of antioxidant enzymes, improving HP & GI conditions and modulation of genes in TBI in vivo.

DMA was effective radioprotector in vivo which exhibited protection against lethal TBI in Balb/c mice at various single DMA doses by oral (p.o.), intravenous (i.v.), intraperitoneal (i.p.) and subcutaneous (s.c.) with dose reduction factor (DRF) of 1.28. It has radioprotective effect in nude mice as well.

In another embodiment the present invention shows that DMA does not exhibit radioprotection in tumor against TBI in tumor bearing mice (TBM). It demonstrated protection of normal tissues against radiation induced damage in TBM. Hence there was increased survival of TBM as compared to irradiated TBM.

The embodiment of the present invention also includes that DMA amileorate radiation induced hematopoietic (HP) and gastrointestinal (GI) system damage. It also recovered HP & GI damage in irradiated TBM. DMA pretreatment to radiation showed increased cell proliferation as compared to irradiated mice only. DMA also regulates radiation induced redox balance in murine.

Another embodiment of the present invention is that DMA showed rapid clearance from plasma when delivered by both oral and i.v. routes of administration. It has preferential accumulation in small intestine.

In the other embodiment it showed that DMA regulates cell proliferation and apoptosis related genes in intestine of irradiated Balb/c mice. It donot alter cell cycle and regulates Akt/NFκB signalling transduction pathway to render radioprotection in normal mice. Knockdown of Akt and NFκB p65 demonstrated no radioprotection by DMA and thus confirming the Akt/NFκB axis as modulatory pathway for radioprotection.

Figure 1:
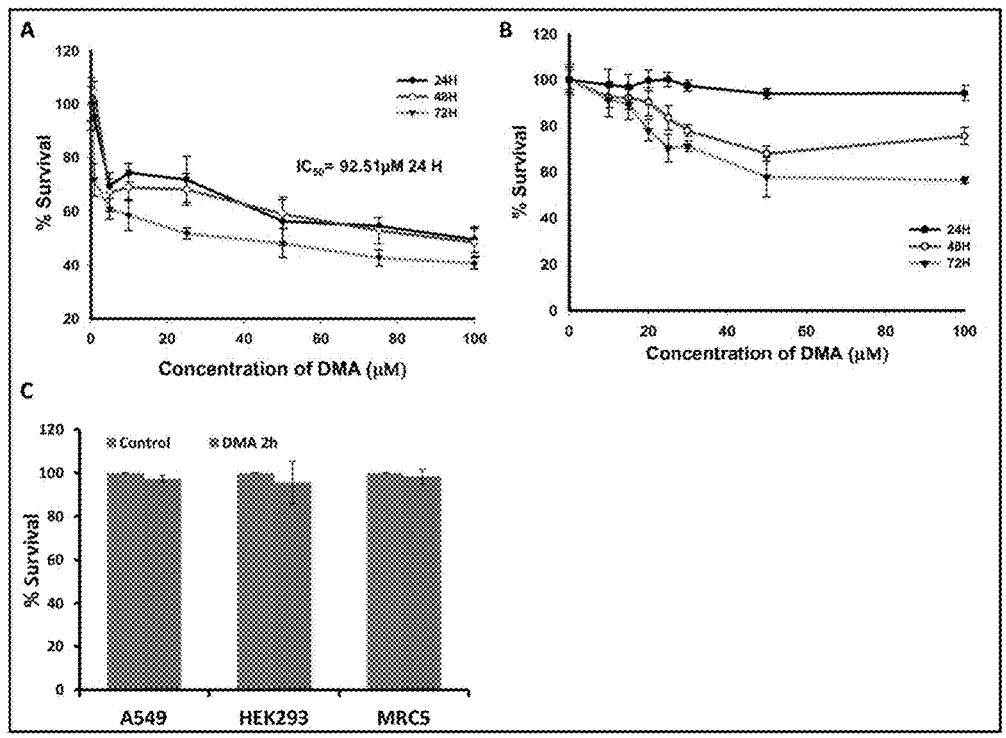
FIG. 1. Cytotoxicity of DMA in Cell Lines. Cytotoxic effect of varying concentration of DMA by MIT assay on A) MRC5 cell line, B) A549 cell line and C) 2 h toxicity effect of 50 μM DMA on A549, HEK293 and MRC5 cell lines. Values are mean (±SD) of three independent experiments.

One of the embodiments also shows that DMA donot activates Akt/NFκB pathway in tumor tissues of TBM against radiation and thus do not offer radioprotection in tumor tissues. Cytotoxicity of DMA against MRC5 and A549 cells over a wide range of concentrations (1-100 µM) up to 72 h post treatment was determined. IC$_{50}$ of DMA with MRC-5 cells was 92.51 µM at 24 h while it could not be achieved in case of A549 cell line up to 72 h (FIGS. 1A & B). DMA was cytotoxic to HEK293 at 50 µM as determined in the inventors' laboratory. Later the inventors performed all in vitro experiments at 50 µM DMA treatment for 2 h before radiation for uniform treatment condition and effective radioprotection, it was necessary to evaluate the toxicity of DMA after 2 h incubation. There was no observable $IC_{50}$ at 2 h short term incubation of 50 μM DMA in A549, HEK293 and MRC5 cell lines which was most effective concentration of DMA providing significant radioprotection (FIG. 1C).

Figure 2:
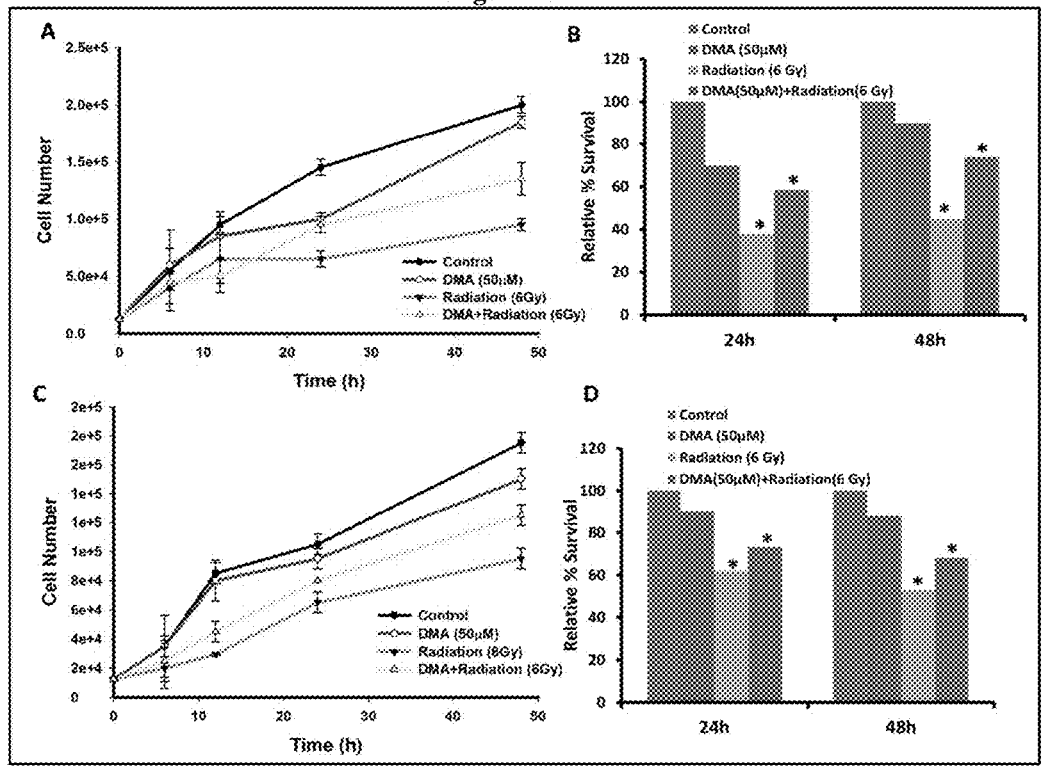
FIG. 2. Radioprotection by DMA Against Radiation in MRC5 and A549 Cell Lines. A) Proliferation of viable MRC5. B) Graphical representation of % survival of MRC5 cell line at 24 and 48 h C) A549 treated with 50 μM DMA in presence and absence of 6 Gy radiation and D) Graphical representation of % survival of A549 cell line at 24 and 48 h. Cell numbers were determined by haemocytometer at 0, 6, 12, 24 and 48 h. Values are mean (±SD) of three independent experiments. *p<0.05 compared to the control group.

Similarly in response to irradiation (6 Gy), there was 37.93% growth in MRC5 cells and 61.90% in A549 cells at 24 h while at 48 h it was 45% of growth in MRC5 and 53.10% in A549 in radiation-treated cells compared to the untreated. However, cells treated with DMA prior to irradiation showed better growth than radiation only cells, i.e., 58.62% in MRC5 and 73% in A549 cells at 24 h and 74% in MRC5 and 68% in A549 cells at 48 h compared to control. There was 20.69% radioprotection at 24 h and 29% at 48 h in MRC5 whereas 11.1% at 24 h and 15% at 48 h in A549 cells (FIGS. 2A, B, C & D).

Figure 3:
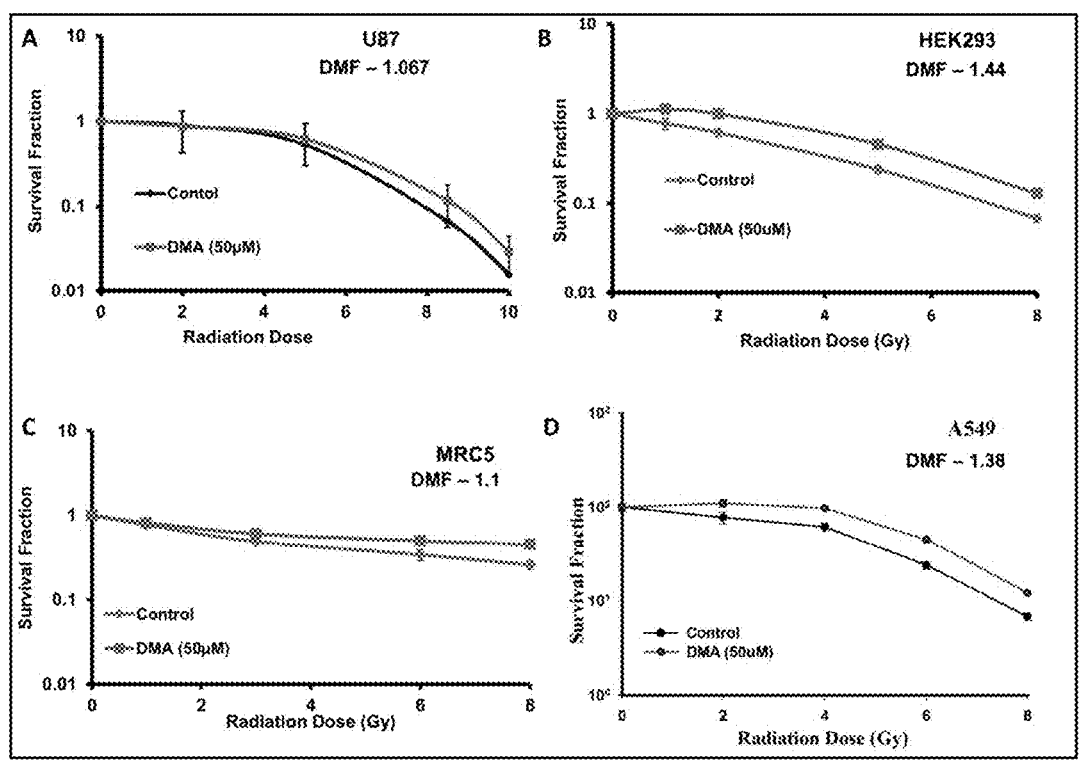
FIG. 3. Radioprotection and DMF of DMA in cell lines. Clonogenic survival of A) U87, B) HEK293, C) MRC5 and D) A549 cell lines at 50 μM DMA treatment for 2 h followed by radiation at indicated doses. Petri dish were incubated for 7-10 days depending upon colony formation. Platinf efficiency and survival fractions were calculated. DMF was reported at 50% survival of DMA+Radiation and radiation conditions. Values are mean (±SD) of three independent experiments.

One of the embodiments relates to estimate the efficacy of radioprotector in cell lines, DMF is standard indicator of radioprotector. The inventors performed the clonogenicity and determined DMF at 50% survival to know efficacy in cell lines. These cell lines models were selected to cover all sets of conditions and effect of radiation occurring on them. U87 cell is grade IV glioblastoma cell line which is most resistant to radiation. HEK293 is near normal cell line whereas MRC5 is normal lung fibroblast cell line. A549 is lung adenocarcinoma cell line with normal p53 status. DMA demonstrated 1.44 DMF in HEK293 which stands out best among all the cell line used whereas it was least in U87 with 1.07. It was 1.38 in A549 whereas it was only 1.1 in MRC5 (FIGS. 3A, B, C & D).

Figure 4:
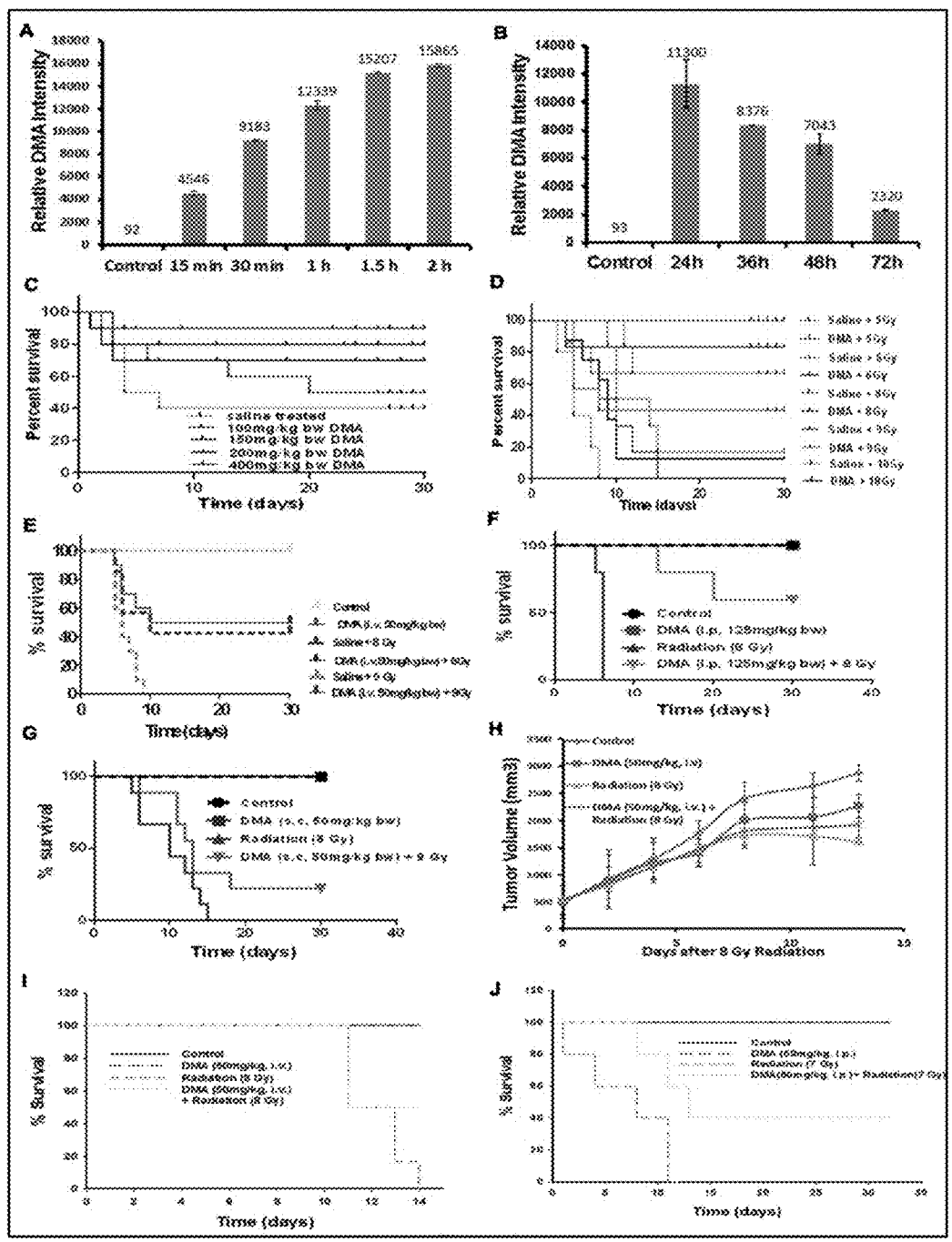
FIG. 4. In vivo radioprotection by DMA. (A) Flow cytometric analysis (FCA) of 50 μM DMA stained unfixed HEK293 cells after 15, 30 min, 1, 1.5 and 2 h. (B) HEK293 cells were incubated with 50 μM DMA for 2 h, washed and cells were collected after 24, 36, 48 and 72 h for FCA. Values are mean±SD of three independent experiments. (C) Survival plots at 100, 150, 200 and 400 mg/kg DMA treatment of Balb/c mice at 8Gy TBI (n=6/group). % survival of mice at (D) 5, 6, 8, 9 and 10Gy TBI, with or without oral 200 mg/kg DMA pre-treatment (n=10/group), (E) 8 and 9Gy TBI, with or without 50 mg/kg, i.v. DMA pretreatment (n=10/group), (F) 8 Gy TBI, with or without 125 mg/kg, i.p. DMA pretreatment (n=10/group), (G) 8 Gy TBI, with or without 50 mg/kg, s.c. DMA pretreatment (n=10/group), (H) Effect of 50 mg/kg i.v. DMA on 8Gy TBI treated melanoma bearing Balb/c mice. Tumor volumes were measured until animals died. (I) % survival of TBM after 8Gy TBI, with or without 50 mg/kg, i.v. DMA pretreatment (n=6/group). (J) 7Gy TBI with or without 50 mg/kg, i.p. DMA pretreatment on nude mice (n=5/group) *P value <0.05 as compared to control was considered significant.

In another embodiment it was observed that DMA reached its highest intensity at 2 h in cells but DMA intensity reduced gradually in cells in next 72 h as observed by flow cytometry analysis. This prolonged DMA intensity was due to more tight binding and may be longer retention of DMA with DNA. The relative maximum uptake intensity of DMA at 2 h by flow cytometry was in line with live cell imaging data whereas nearly 14% relative DMA intensity could be detected from HEK293 cells till 72 h (FIGS. 4A & B). Mice pre-treated orally to 8Gy TBI with normal saline, 100, 150, 200 and 400 mg/kg DMA doses exhibited 30-days survival rates of 38, 54, 70, 80 and 90% respectively when compared to radiation (FIG. 4C). Therefore 200 mg/kg DMA oral dose was selected as effective radioprotective dose. Further, control mice given saline alone displayed 30-day survival rates of 70, 70, 38, 0 and 0% when irradiated with 5, 6, 8, 9 and 10Gy respectively. However, pre-treatment with DMA at 200 mg/kg showed survival rates of 100, 100, 82, 18 and 12% when irradiated with 5, 6, 8, 9 and 10Gy respectively (FIG. 4D) with 1.28 dose reduction factor (DRF). 50 mg/kg i.v. administration of DMA 2 h prior to 8Gy TBI exhibited 100% radioprotection in mice as compared to only 8Gy irradiated mice which showed 40% survival (FIG. 4E). 50% mice survived at 9Gy with DMA pretreatment to irradiation (FIG. 4E) with no survival in radiation only. When 125 mg/kg DMA was administration through i.p. 2 h before 8Gy radiation, there was 55% mice survival whereas there was no survival after 8 days in TBI mice (FIG. 4F). Similarly 20% radioprotection was observed when 50 mg/kg DMA was administered s.c. 3 h prior to 8Gy TBI (FIG. 4G). Gradual weight loss was observed in TBI mice. However, mice pre-treated with DMA showed considerable weight regain after initial 9 days of radiation with delayed appearance of radiation sickness. DMA by itself had no effect on rodents.

DMA does not Protect Tumor Cells Against Radiation

One of the embodiment of the present invention is that DMA does not protect tumor cells against radiation. Systemic administration of DMA at 50 mg/kg, 2 h before irradiation in melanoma model of Balb/c mice showed less radioprotection to tumor tissues (FIG. 4H). There was 50% survival of melanoma bearing Balb/c mice in prior DMA treated mice as compared to 16.6% at 13th day and 0% on 14th day in 8Gy TBI mice (FIG. 4I). Similarly at 300 mg/kg DMA oral dose showed radioprotection of normal cells where as no protection to tumor tissues (Nimesh et. Al 2015).

DMA Render Radioprotection in Nude Mice

In another embodiment of the present invention it was investigated that DMA render radioprotection in nude mice. The inventors investigated survival of nude mice by DMA against lethal radiation dose to access translational advances of DMA. There was no survival of nude mice after day 12 at 7Gy TBI whereas 40% nude mice survived 30-days when DMA (50 mg/kg, i.p.) was administered 2 h prior to radiation (FIG. 4J).

DMA Pretreatment Ameliorates Radiation Induced Tissue Damage

Figure 5:
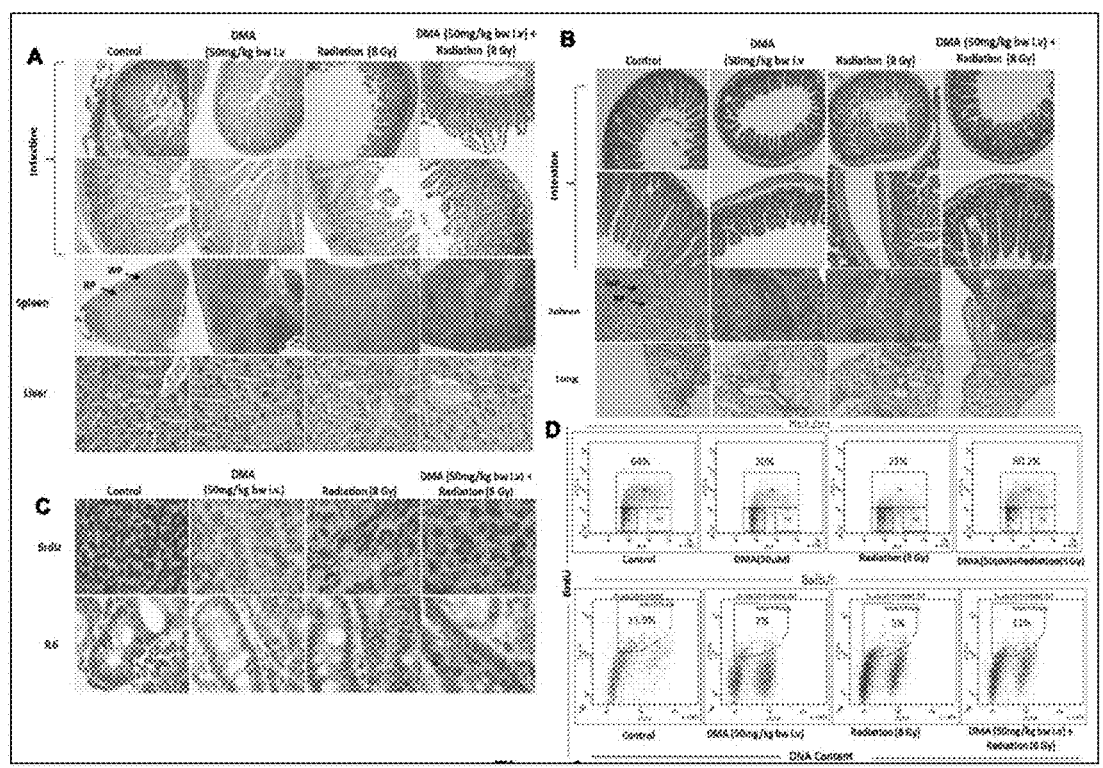
FIG. 5. Histological demonstration of radioprotective effect of DMA. Tissue sections performed 3 days postirradiation (8Gy) with and without 50 mg/kg bw, i.v. DMA pretreatment with the control and DMA treated tissues (A) Images showing spleen, intestine and liver analysis at magnification 40× objective lens. (B) Small intestine, spleen and lung sections from melanoma tumor bearing mice at 40× & 60× objective lens (C) Immunohistochemical analysis of BrdU uptake in spleen and IL6 protein expression in intestine tissues at 100× objective lens magnification. (D) Graphical representation of actively proliferating HEK293 at 48 h and Balb/c intestinal cells by BrdU uptake under each condition (n=3/group from 2 independent experiments).

Another embodiment of the present invention relates to DMA pretreatment improves radiation induced tissue damage. Control and DMA (50 mg/kg, i.v.) treated mice intestine tissue showed normal villi structures and muscularies (FIG. 5A). Disruption of villi architecture and crypts were observed in 8Gy TBI animals' intestines (FIG. 5A). DMA pretreatment to irradiation restored the crypts and villi architecture with villi height almost equivalent to control group. There was white pulp loss in spleen of irradiated mice whereas it appeared normal in control and DMA treated groups. DMA pretreatment to radiation restored the white pulp in spleen (FIG. 5A). Liver histology in the radiation indicated fragmentation of hepatocytes showing pyknotic and inflammatory kupffer cells. Hepatocytes appeared normal in control and DMA groups. There was reduction in the number of pyknotic and inflammatory kupffer cells in DMA pretreated to radiation group (FIG. 5A). These data clearly exhibit the radioprotective ability of DMA to mitigate radiation induced tissue damages.

DMA Pretreatment Reduces Radiation Induced Normal Tissue Damage in Tumor Bearing Mice Another embodiment of the present invention relates to that DMA pretreatment reduces radiation induced normal tissue damage in tumor bearing mice. Spleen showed structural retention through white and red pulp protection in DMA (50 mg/kg, i.v.) treated melanoma TBM as compared to 8Gy TBI mice (FIG. 5B). Intestine amelioration was exhibited with intact better heighted villi and crypts in DMA pretreated TBM to radiation (FIG. 5B). Lung demonstrated distorted alveolar structure in TBI mice which was less destructured in DMA treated TBM prior to radiation (FIG. 5B). The irradiated mice mortality was due to both tumor load and radiation induced damage to HP and GI systems. Load of tumor was prime mortality factor in DMA pretreated TBM to radiation as there was radioprotection of HP & GI system and thus longer survival as compared to TBI mice.

DMA Regulates Proliferation and Apoptosis in Irradiated Balb/c Mice Intestine Tissue In another embodiment of the present invention it was observed that DMA regulates proliferation and apoptosis in irradiated Balb/c mice intestine tissue. There were more BrdU-positive cells in DMA+Radiation as compared to irradiated Balb/c mice intestine tissue (FIG. 5C). There was higher level of IL6 in DMA+Radiation as compared to irradiated mice small intestine tissue, comparable to untreated control. Level of IL6 in DMA only treated mice was almost equal to control mice (FIG. 5C).

Cell proliferation was significantly enhanced by DMA (50 mg/kg, i.v.) pretreatment to radiation as compared to radiation. Cell proliferation was same in control and DMA treated mice intestine tissue. There was 5% active S-phase cells in 8Gy TBI Balb/c mice whereas it was 11% in DMA pretreated animal (FIG. 5D). Similarly, we found that DMA enhances proliferation in HEK293 cells. 60% and 30% cells were at active S phase in control and DMA treated cells respectively at 48 h. S phase cells reduced drastically in 5Gy irradiated cells which came back to normal in DMA+Radiation and was comparable to control cells (FIG. 5D).

DMA Exhibits Protection of HP System in Balb/c Mice

In one of the embodiments of the present invention DMA exhibits protection of HP system in Balb/c mice. A significant reduction in spleen index was observed in TBI animals (0.21±0.06) compared to control (0.40±0.09). Pretreatment with DMA (200 mg/kg, oral) improved the spleen index (0.33±0.02) compared to radiation. DMA treatment exhibited 0.41±0.05 spleen index. Significant increase in endogenous colony forming units on $10^{th}$ day post-irradiation was observed in DMA+Radiation (11.25±1.7) compared to radiation (5.25±1.5) (FIG. 6A) which suggests protection of HP cells.

DMA Regulates Radiation Induce Redox Balance in Murine

Another embodiment of the present invention shows that DMA regulates radiation induce redox balance in murine. Oral DMA (200 mg/kg) administration resulted in insignificant change (0.19±0.06) in MDA level compared to control group (0.22±0.03) in hepatic tissues. 8Gy TBI induced a significant increase in MDA level (0.76±0.29) compared to control group at 24 h post-irradiation. DMA pre-treatment significantly decreased the MDA level (0.20±0.04) as compared to radiation (FIG. 6B) thus restoring the damage caused by lipid peroxidation.

Insignificant change in reduced glutathione (GSH) levels was observed in mice liver treated with DMA (200 mg/kg, oral) (5.07±0.09) as compared to control animals (5.69±0.26) (FIG. 6C). 8Gy TBI resulted in significant decrease in GSH levels (2.16±0.34) whereas pre-treatment with DMA significantly restored the GSH levels in mice liver tissues (3.73±0.69) as compared to radiation control.

Figure 6:
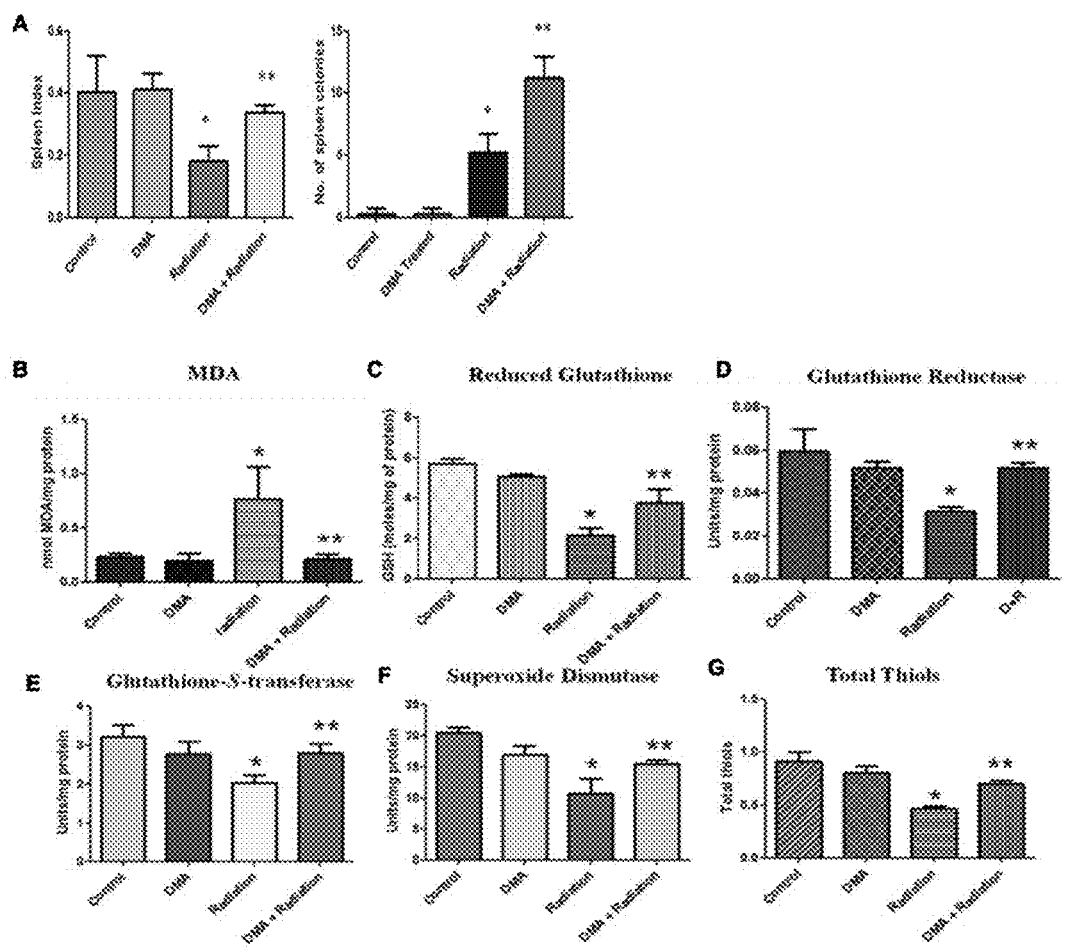
FIG. 6. DMA regulated radiation induced damages in murine. (A) Effect of DMA (200 mg/kg, oral) on spleen excised 10 days after 8Gy irradiation in Balb/c mice (n=6). Bar graphs show comparison of spleen index among different groups; and comparison of number of spleen colonies among different groups. *P value <0.05 as compared to saline control; **P value <0.05 as compared to radiation control. Effect of DMA (200 mg/kg bw), radiation (8Gy) and their combination on the level of (B) malondialdehyde (MDA) (C) reduced GSH. (D) GR Activity (E) GST Activity (F) SOD and (G) total thiol content in Balb/c mice liver tissue. Error bars are standard deviation (SD) for n=6. *P value <0.05 as compared to saline control; **P value <0.05 as compared to radiation control.

Radiation induced increase in the activity of glutathione reductase compared to control group (FIG. 6D). Treatment with DMA 2 h prior to irradiation resulted in a significant decrease in enzyme activity compared to irradiated group. γ-Irradiation induced significant decrease (2.02±0.20) in GST level while treatment with DMA (200 mg/kg, oral) resulted in insignificant decrease (2.76±0.32) in GST level compared to the control group (3.20±0.30). Administration of DMA prior to radiation induced significant increase (2.78±0.25) in GST content compared to irradiated group (FIG. 6E). DMA did not show any significant change (16.96±1.35) in SOD activity whereas 8Gy TBI induced significant decrease (10.68±2.4) compared to control group (20.49±0.83) (FIG. 6F). Increased levels of SOD with DMA pre-treatment to radiation (15.50±0.60) showed protection of the mice from the acute radiation effects.

TBI showed a significant decrease in total thiol contents (0.47±0.02) in mice liver homogenates as compared to control tissues (0.81±0.05) (FIG. 6G) which was restored by DMA pre-treatment (0.91±0.08) indicates maintenance of desired level of SH groups.

Rapid Clearance of DMA from Plasma

Figure 7:
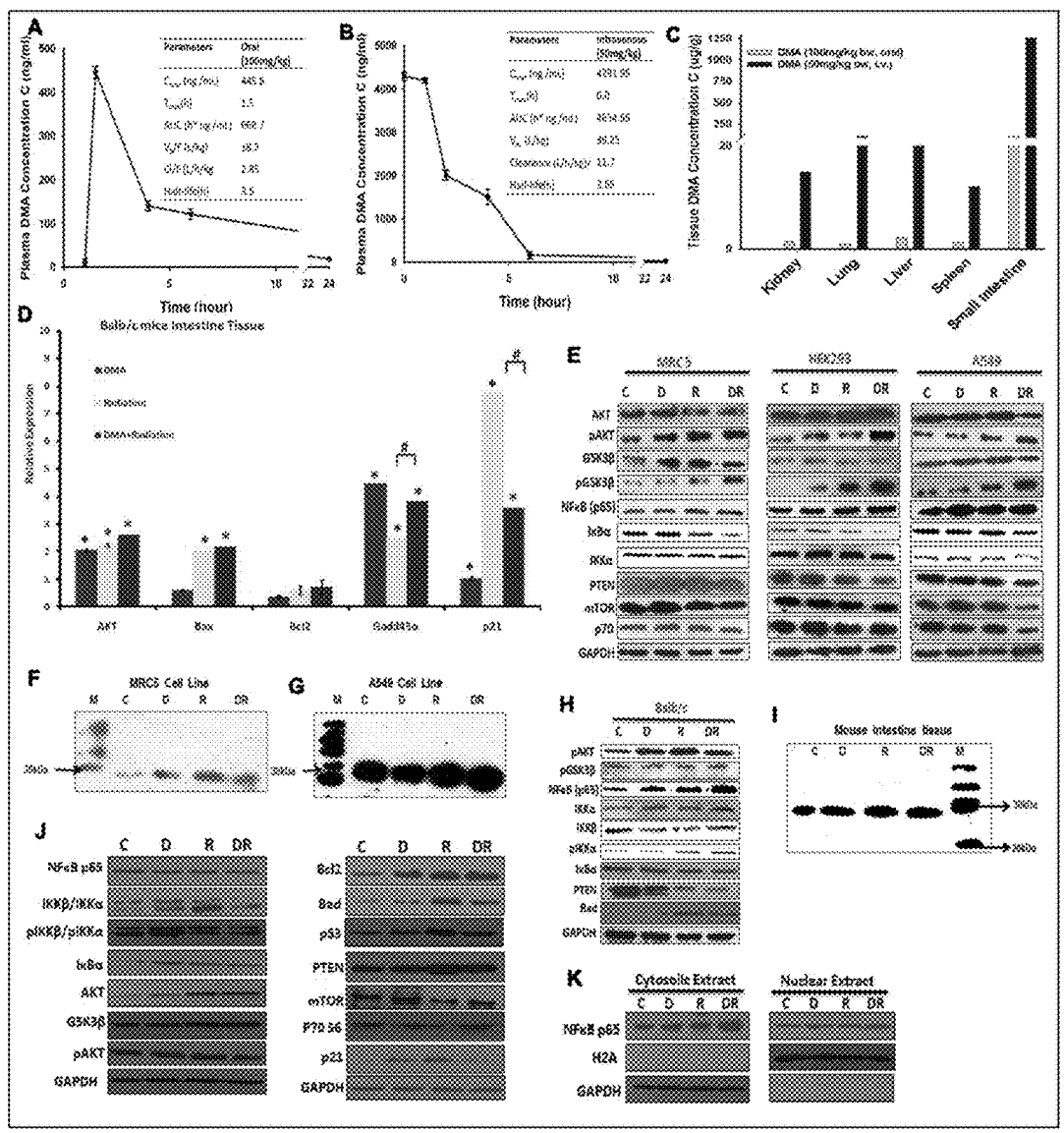
FIG. 7. Pharmacokinetic and mechanistic analysis of DMA. DMA concentration in plasma from Balb/c mice following (A) 100 mg/kg oral administration (B) 50 mg/kg, i.v. (C) Bio-distribution of DMA (100 mg/kg, oral and 50 mg/kg, i.v.) in tissues at the point of maximum concentration in respective organs (n=3/tissue/timepoint). (D) Effect of DMA on the mRNA expression of Akt, Bax, Bcl-2, Gadd45, and p21 genes from Balb/c mice intestine tissue (n=3) .*p<0.05 compared to the control group, #p<0.05 compared to the irradiated group. (E) Western blot analysis of indicated proteins from whole cell protein from MRC5, A549 and HEK293 cells. Akt kinase assay as per manufacturer's instruction from (F) MRC5 cells, (G) A549 cells (H) Western blot analysis of indicated proteins and (I) Akt kinase assay from mice intestine tissue (n=3). (J) Western blot analysis of indicated proteins from melanoma tissue of mice (n=3). (K) Western blot analysis of indicated proteins from cytoplasmic and nuclear HEK293 cells extract where C denotes Control, D denotes 50 mg/kg i.v. and 50 µM for cells, R denotes 5Gy for HEK293, 6Gy for MRC5 and A549 cell lines and 8Gy TBI in Balb/c mice. DR denotes DMA+ Radiation as mentioned previously. Data represented as mean±SD for each time point from 3 independent experiments.

The plasma concentration of DMA (100 mg/kg, oral) achieved peak value of 445.8 ng/ml at 1.5 h and declined to basal level in 16 h. It suggested rapid absorption and distribution of DMA to the different tissues followed by its elimination (FIG. 7A). It took 1.5 h to reach its maximum concentration ($t_{max}$) with 668.7 h ng/ml area under curve (AUC) for oral DMA dose and half-life was 3.5 h. The other parameters are listed in FIG. 7A. When DMA was delivered at 50 mg/kg i.v. the maximum concentration observed was 4291.95 ng/ml with 2.65 h half-life (FIG. 7B) predicting rapid absorption by tissue or faster elimination. The volume of distribution (Vss) of DMA is larger than the total blood volume of mouse (FIG. 7B) indicating that the compound is readily distributed in extravascular system. However, the systemic clearance of DMA is higher (11.7 L/h/kg) than the hepatic blood flow of the mouse (5.4 L/h/kg) indicating an extrahepatic elimination of the compound.

DMA Preferentially Accumulates in Small Intestine

DMA accumulation in different tissues as function of time is important parameter to predict the preferred action site of DMA in the body. Maximum concentration of DMA reached was 106 µg/g in small intestine at 2 h, 2.23 µg/g in liver followed by 1.53 µg/g in kidney both at 4 h and 1.31 µg/g in spleen at 2 h when administered orally at 100 mg/kg. The concentration of DMA reached in lung was 1 µg/g at 4 h. Thus following single oral DMA dose in the mouse, the concentration was in the order of $C_{intestine} > C_{liver} > C_{kidney} > C_{spleen} > C_{lungs}$ (FIG. 7C). When 50 mg/kg DMA was administered i.v., DMA concentrations achieved were 1260 µg/g in intestine, 109 µg/g in lung, 41.6 µg/g in liver, 14.9 µg/g in kidney followed by 12.1 µg/g in spleen. The concentration was in the order of $C_{intestine} > C_{lungs} > C_{liver} > C_{kidney} > C_{spleen}$ (FIG. 7C). DMA was preferentially accumulated in small intestine with 11.88 fold concentration through i.v. as compared to oral route suggesting it as radioprotector of GI system. All detailed parameters of DMA tissue biodistribution by both routes of administration are provided in table 1, 2 & 3.

TABLE 1

Tissue concentration-time profile of DMA after oral (100 mg/kg) and intravenous (50 mg/kg) administration in Balb/c mice

| Time | Tissue DMA concentration (ng/g of tissue) | | | | | | | | | |
|---|---|---|---|---|---|---|---|---|---|---|
| | Liver | | Spleen | | Lung | | Kidney | | Intestine | |
| (h) | Oral | i.v | Oral | i.v | Oral | i.v | Oral | i.v. | Oral | i.v. |
| 1 | 161 | 41600 | 401 | 6970 | 211 | 109000 | 342 | 14900 | 675 | 1260000 |
| 2 | 415 | 2000 | 1310 | 6450 | 436 | 2340 | 1020 | 8370 | 106000 | 70400 |
| 4 | 2230 | 30100 | 681 | 2090 | 1000 | 1770 | 1530 | 9080 | 30200 | 59200 |
| 6 | 735 | 40100 | 558 | 12100 | 538 | 1340 | 643 | 707 | 28700 | 29700 |

TABLE 1-continued

Tissue concentration-time profile of DMA after oral (100 mg/kg) and intravenous (50 mg/kg) administration in Balb/c mice

| Time | Liver | | Spleen | | Lung | | Kidney | | Intestine | |
|---|---|---|---|---|---|---|---|---|---|---|
| (h) | Oral | i.v | Oral | i.v | Oral | i.v | Oral | i.v. | Oral | i.v. |
| 16 | 691 | 22200 | 254 | 9600 | 188 | 993 | 193 | 263 | 612 | 2530 |
| 24 | 192 | — | — | — | — | 730 | — | — | 410 | 1710 |

Values are means ± SEM (n = 3/timepoint/tissue)

TABLE 2

Pharmacokinetic parameters of DMA after 100 mg/kg oral dose in Balb/c mice

| Parameters | Liver | Spleen | Kidney | Small Intestine |
|---|---|---|---|---|
| $C_{max}$ (ng/g) | 2230 | 1310 | 1530 | 106000 |
| $T_{max}$ (h) | 4 | 2 | 4 | 2 |
| AUC (h * ng/g) | 20717.3 | 8353.819 | 10874.29 | 361353.4 |
| Half life (h) | 4.0 | 4.2 | 2.5 | 1.9 |
| $V_d/F$ (g/kg) | 27800 | 71770 | 33200 | 639.8 |
| Cl/F (g/h/kg) | 4000 | 11000 | 9190 | 277 |

Values are means ± SEM (n = 3/timepoint/tissue)

TABLE 3

Pharmacokinetic parameters of DMA after 50 mg/kg intravenous administration in Balb/c mice

| Parameters | Liver | Lung | Spleen | Kidney | Small Intestine |
|---|---|---|---|---|---|
| $C_{1\,hr}$ (ng/g) | 41600 | 109000 | 6970 | 14900 | 1260000 |
| AUC (h * ng/g) | 889040 | 2674622.2 | 145191 | 945577.2 | 220072.6 |
| $V_{ss}$ (g/kg) | 496.11 | 10.72 | 4114.6 | 1623.5 | 4.9 |
| $V_d$ (g/kg) | 668.7 | 552.1 | 3857.9 | 1944.8 | 40360.3 |
| Clearance (g/h/kg) | 39.5 | 18.5 | 89.3 | 17.9 | 15.0 |

Values are means ± SEM (n = 3/timepoint/tissue)

DMA Regulates Cell Proliferation and Apoptosis Related Genes in Balb/c Mice Intestine Tissue In one of the embodiment of the present invention it is observed that DMA regulates cell proliferation and apoptosis related genes in Balb/c mice intestine tissue. There was higher expression of Akt in DMA (50 mg/kg, i.v.)+Radiation (8Gy TBI) condition with respect to control in intestine tissue. DMA, by itself, significantly increased the expression of Gadd45α whereas it did not increase the expression level of Bax, Bcl-2 and p21. Radiation substantially upregulated p21 whereas there were increment in Gadd45α and Bax levels (FIG. 7D). DMA pretreatment (50 mg/kg, i.v.) to radiation significantly downregulated the p21 expression but remained high as compared to control mice. It augmented Gadd45α expression. Antiapoptotic gene Bcl-2 showed downregulation whereas proapoptotic gene Bax exhibited increment in irradiated group. There was no significant downregulation in Bax gene expression though there was insignificant increase in Bcl-2 level in DMA pre-treated to radiation group (FIG. 7D).

DMA Activates Akt/NFκB in Presence of Radiation In Vitro as Well as Balb/c Mice Intestine In another embodiment of the present invention it was observed that DMA activates Akt/NFκB in presence of radiation in vitro as well as Balb/c mice intestine. To elucidate the underlying molecular mechanism of DMA in radioprotection, the present study was planned. There was no change in Akt protein level on DMA treatment, whereas the level of phosphorylated Akt (Ser-473) was increased in DMA+Radiation condition in HEK293, MRC5 and A549 cell lines. The Akt pathway activation was confirmed by increase in phosphorylated GSK3β in the cells with prior DMA treatment to radiation, while the GSK3β showed no change in expression level in all three cell lines (FIG. 7E). There was increased level of NFκB p65 in DMA+Radiation as compared to control and irradiated conditions. The phosphorylation of both IKKα and IKKβ were higher in DMA+Radiation condition whereas basal level remained constant in all conditions in all three cell lines. There was decrease in protein level of IκBα in DMA+Radiation case in all three cell lines. To check the effect of other related and converging pathway of Akt, we monitored the level of mTOR, p70, and PTEN. We could not address any significant changes in PTEN, mTOR and p70 in all three cell lines (FIG. 7E). We performed Akt Kinase assay to ascertain the role of Akt in offered radioprotection by DMA in cell lines. We observed higher Akt kinase activity in DMA+Radiation condition in MRC5 and A549 as compared to control and radiation (FIGS. 7F & G). In agreement with in vitro data, we observed higher level of phosphorylated Akt, GSK3β and IKKα/β in DMA treated intestine tissue prior to irradiation whereas basal level remained almost constant in all conditions (FIG. 7H). We observed higher expression of NFκB p65 in DMA+Radiation condition. IκBα level was lower in radiation and DMA+Radiation conditions. There was significant reduction in PTEN level in both radiation and DMA+Radiation condition in Balb/c mice intestine tissue, whereas higher level of Bad in irradiated mice as compared to DMA+Radiation treated mice was observed (FIG. 7H). Similarly we observed higher kinase activity of Akt in DMA+Radiation condition in intestine as compared to control and radiation (FIG. 7I).

DMA does not Modulate Akt/NFκB in Tumor Tissue

In the other embodiment it was observed that DMA does not modulate Akt/NFκB in tumor tissue. To investigate the effect of DMA on Akt/NFκB pathway activation against radiation in tumor tissues, TBM were treated with DMA (50 mg/kg, i.v) followed by 8Gy TBI. The level of NFκB p65 was same in tumor tissues of control, DMA and Radiation conditions with lower expression in DMA+Radiation condition. Similarly IKK (both basal and phosphorylated form) was same in 3 conditions and downregulated in DMA pretreatment to radiation condition (FIG. 7J). IκBα was downregulated in control tumor tissue whereas its expression was similar in all three remaining conditions. Though there was increased basal level of Akt and GSK3β in all 3 conditions as compared to control, phosphorylated Akt level was similar in control, DMA and irradiated conditions and lower in DMA pretreated to irradiation of TBM. Bcl2 was overexpressed in all three conditions as compared to control tumor tissue but the expression of apoptosis protein Bad was high in both irradiated tumor tissues (FIG. 7J). p53 was found to be overexpressed in irradiated tumor and was almost similar in expression in other three conditions. p21 was found to be upregulated in DMA only treated and irradiated conditions as compared to control and DMA+ Radiation conditions (FIG. 7J). PTEN was found to be overexpressed in both irradiated conditions as compared to control and DMA only treated conditions. There were no observable changes in protein expression of mTOR and p70S6 in all conditions (FIG. 7J). These results clearly showed that DMA does not modulate Akt/NFκB signaling in response to radiation in tumor tissues which was activated in case of mammalian cell lines and Balb/c mice.

We determined the localization of NFκB p65 in cytoplasm and nucleus in response to DMA. There was higher expression of NFκB p65 in cytoplasm and nucleus in DMA prior treated to radiation cells as compared to control, DMA and irradiated conditions (FIG. 7K). Hence this translocation of NFκB in nucleus clearly suggests transcriptional activation of the downstream targets of NFκB gene and thus regulated the cell proliferation and prosurvival pathways.

DMA does not Alter the G2/M Checkpoint In Vitro

Figure 8:
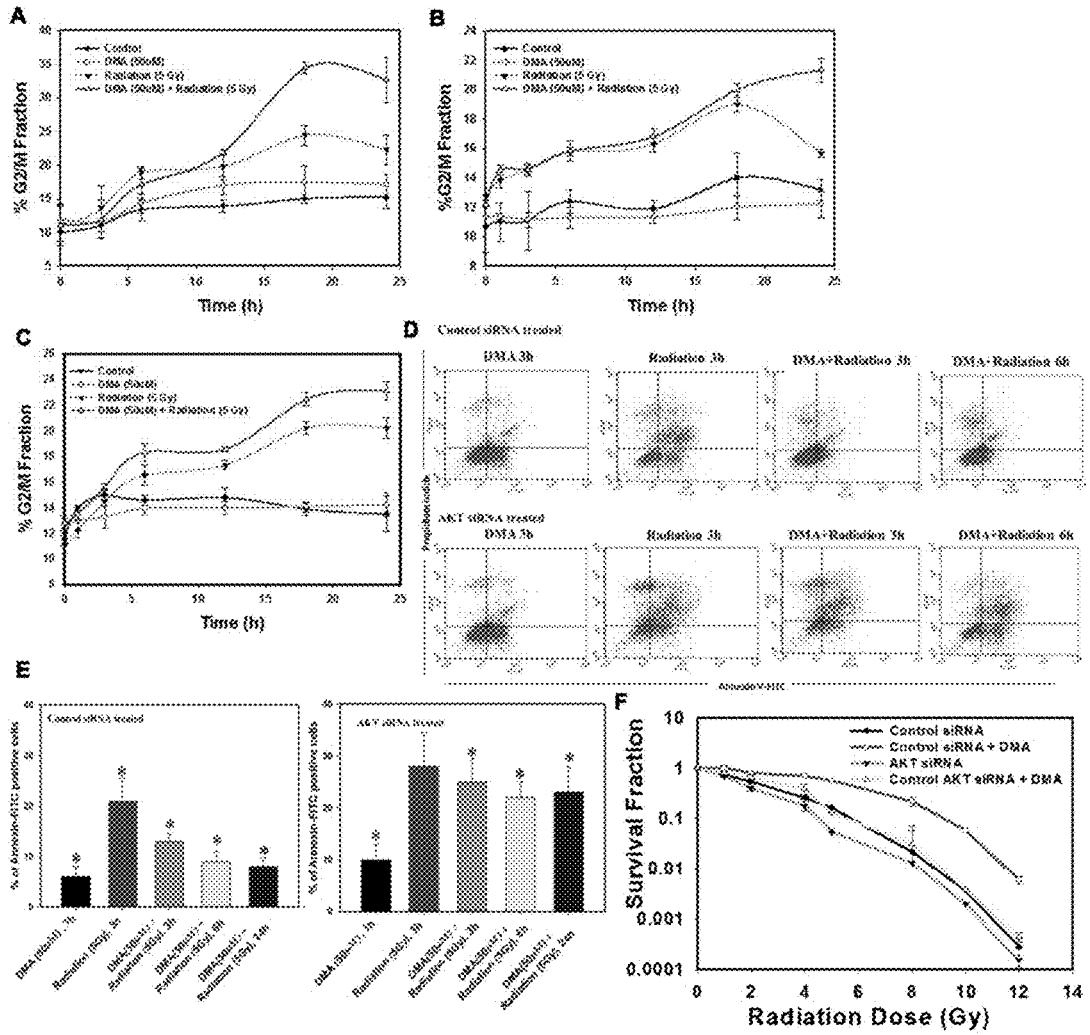
FIG. 8: Akt depleted HEK293 cells do not exhibit Radioprotective effect of DMA. Cell cycle progression showing % G2-M fraction at 0, 1, 3, 6, 12, 18 and 24 h (A) Control HEK293 cells with 50 µM DMA, radiation (5Gy) and DMA (50 µM)+Radiation (5Gy). (B) control siRNA transfected HEK293 cells (C) Akt siRNA transfected HEK293 in 50 µM DMA, radiation (5Gy) and DMA (50 µM)+Radiation (5Gy). (D) Apoptosis analysis of control siRNA and Akt siRNA transfected HEK293 cells at 3 h, 6 h in 50 µM DMA, radiation (5Gy) and DMA (50 µM)+Radiation (5Gy). (E) % Annexin V$^+$ and Annexin V$^+$PI$^+$ cells in control siRNA and Akt siRNA transfected HEK293 cells at, 3 h, 6 h and 24 h in 50 µM DMA, radiation (5Gy) and DMA (50 µM)+ Radiation (5Gy)(Data Not shown for 6 h and 12 h (F) Clonogenic survival assay of only control siRNA transfected cells, 50 µM DMA treated control siRNA transfected cells, only Akt siRNA transfected cells, and 50 µM DMA treated Akt siRNA transfected cells treated at different radiation doses. Error bars are SEM from 3 independent experiments.

We observed normal cell cycle in DMA treated HEK293 cells (FIG. 8A). There was G2 phase accumulation at 6 h (15%) to 18 h (19%) after exposure to 5Gy which came down to 15.6% at 24 h (FIG. 8A). There was no significant G2 check point observed after DMA (50 µM) treatment in HEK293 cells, but in DMA+Radiation treated cells we have observed a significant G2-M delay at 18 h (FIG. 8A). When cells treated with control siRNA, the cell cycle analysis was same as that of normal cells (FIG. 8B) whereas G2/M accumulation was more in DMA+Radiation treated cells as compared to irradiated HEK293 cells with Akt siRNA treatment (FIG. 8C). The delay in cell cycle progression is probably exploited by the cells to perform DNA repair, and reduce the adverse effects of radiation.

DMA Attenuates Radiation Induced Apoptosis in HEK293 Cells Through Akt Activation In another embodiment of the present invention it was observed that DMA attenuates radiation induced apoptosis in HEK293 cells through Akt activation. Irradiated HEK293 cells showed early and late apoptotic events up to 24 h. In DMA+Radiation treated cells the total number of early and late apoptotic cells (12% at 3 h, 9% at 6 h and 7% at 24 h) were observed less in comparison to radiation in control siRNA treated HEK293 cells {20% at 3 h, (6 and 24 h data not shown)} (FIG. 8D, E). But in Akt knocked down cells the apoptotic events were almost similar as in radiation i.e; 27% at 3 h, (6 and 24 h data not shown) as well as DMA+Radiation treated cells (23% at 3 h, 21% at 6 h, and 22% at 24 h), suggesting that Akt plays a role in the radioprotection activity of DMA (FIG. 8D, E).

Inhibition of Akt and NFκB Limits Radioprotection Abilities of DMA

The other embodiment of the present invention is inhibition of Akt and NFκB limits radioprotection abilities of DMA. In vitro clonogenicity assay results showed significant radiation protection by DMA against radiation in control siRNA transfected cells. The inventors observed minimal radiation protection by DMA in Akt siRNA transfected cells against radiation (FIG. 8F). There was 40.6% radioprotection in control siRNA and 7.5% in Akt siRNA treated cells by DMA at 5Gy.

Figure 9:
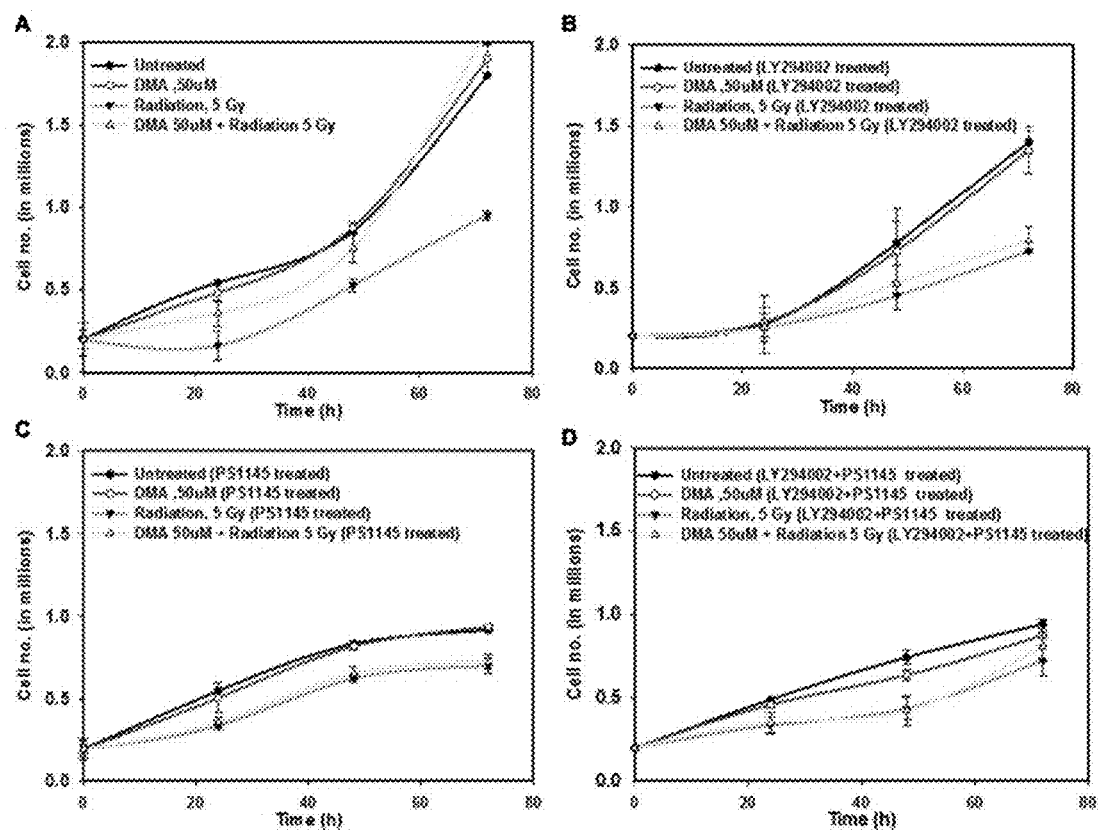
FIG. 9. Cell proliferation in presence of inhibitors. Proliferation kinetics assay in control (no inhibitor treated), only 50 µM LY294002 (Akt inhibitor) and only 10 µM PS1145 (NFkB inhibitor) and both LY294002 and PS1145 treated HEK293 cells (A) HEK293 cells (Control, no inhibitor treated) were treated with 50 µM DMA and 5 Gy Radiation. Post treatment cells were seeded in 60 mm well plates ($2 \times 10^5$ cells per plate) and their proliferation kinetics was studied at 24, 48 and 72 h intervals following trypsinization and counting total cells per well using a hemocytometer. (B) HEK293 cells prior treated with LY290004 were then treated with 50 µM DMA and 5 Gy Radiation. (C) HEK cells prior treated with PS1145 were then treated with 50 µM DMA and 5 Gy Radiation (D) HEK cells prior treated with both LY290004 and PS1145 treated were then treated with 50 µM DMA and 5 Gy Radiation. Values are mean (±SD) of three independent experiments.

In order to confirm the role of Akt and NFκB, we investigated radioprotection by DMA in presence of Akt and NFκB inhibitors in HEK293 cells. The % radioprotection by DMA in control cells (no inhibitor treated) with respect to drug only control at 24, 48 and 72 h was 40%, 35% and 16% respectively (FIG. 9A); in LY294002 treated cells % radioprotection by DMA was reduced to only 15, 10, and 4% at 24, 48 and 72 h respectively (FIG. 9B). In PS1145 treated cells % radioprotection by DMA was reduced to 4, 3.5, and 2.4% at 24, 48 and 72 h respectively (FIG. 9C). When HEK293 cells were treated with both LY294002 and PS1145 simultaneously % radioprotection by DMA was 3, 2.2, and 2% at 24, 48 and 72 h respectively (FIG. 9D). Transient inhibition of Akt and NFκB resulted in no radioprotection by DMA in HEK293 cells.

Figure 10:
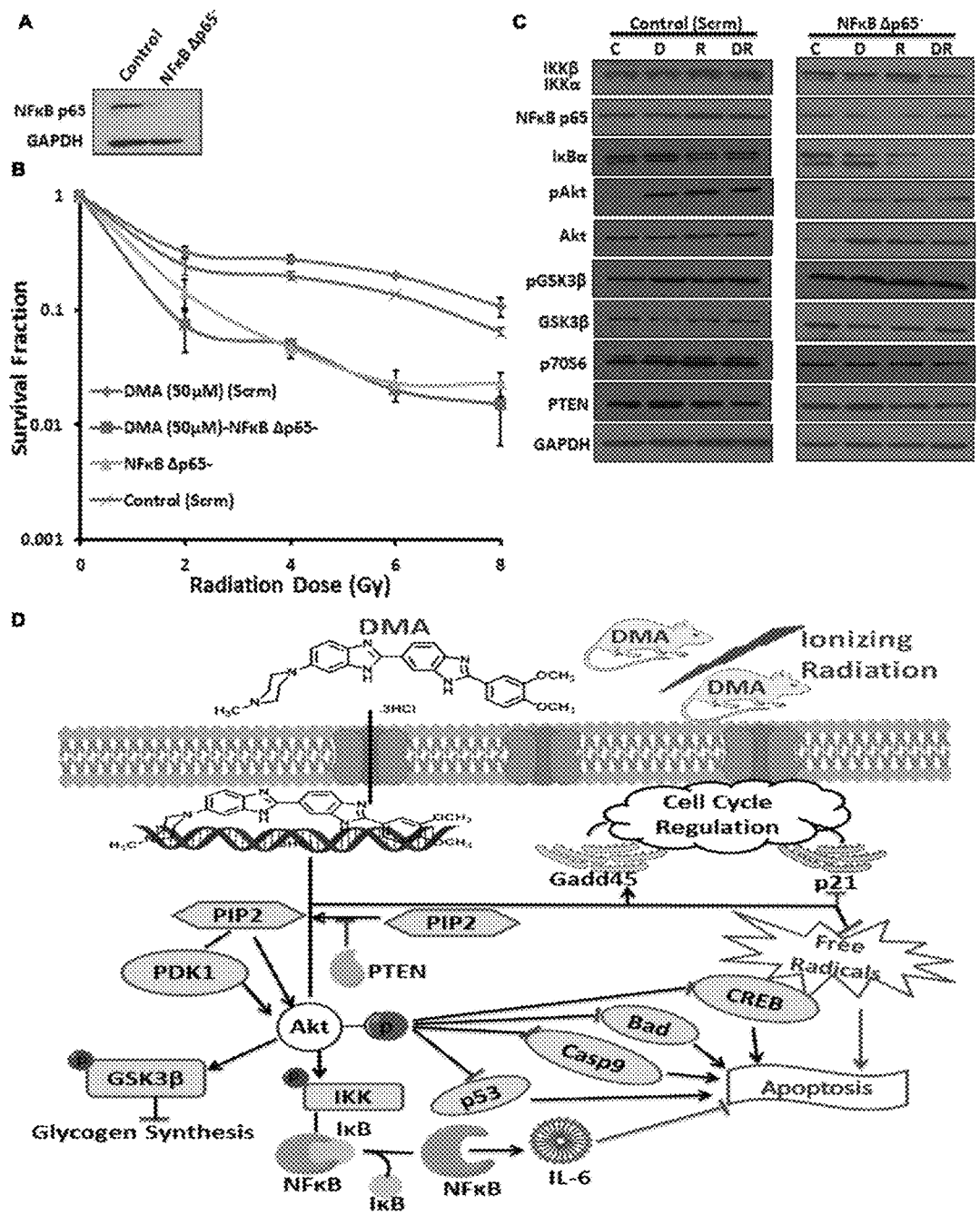
FIG. 10. DMA offer no radioprotective effect in NFκB Δp65$^-$ A549 cell line. (A) Western blot analysis to confirm NFκB Δp65$^-$ in A549 cell line. (B) Clonogenic survival of both scramble A549 (Control scrm) and NFκB Δp65$^-$ A549 with 2 h 50 µM DMA treatment followed by indicated radiation doses. (C) Western blot analysis of indicated proteins in both scramble A549 (Control scrm) and NFκB Δp65$^-$ A549 cells where C denotes Control, D denotes 50 µM DMA, R denotes 6Gy. DR denotes DMA+Radiation as mentioned previously. (D) Schematic representations showing minor groove binder DMA binds to genomic DNA and activates Akt/NFκB signaling pathway to regulate apoptotic pathway. It promotes cell survival and proliferation through amelioration of HP and GI injuries of ARS. It upregulated Gadd45α and downregulated p21 levels to check cell cycle progression in response to radiation

To explore the role NFκB in delivering radioprotection by DMA, we determined radioprotection and expression level of Akt pathway proteins in NFκB p65 knockdown (NFκB Δp65⁻) A549 cell line. The efficacy of knockdown of NFκB p65 was shown in FIG. 10A. There was no radioprotection in NFκBΔp65⁻ cells by DMA with 1.02 DMF in NFκB Δp65⁻ A549 and 1.28 DMF in scrambled sequence transfected A549 cells (FIG. 10B). There was increased expression of pAkt and pGSK3β in both scramble and NFκB Δp65⁻ A549 cells with no change in basal level of both proteins (FIG. 10C). This was in-line with our previous results on MRC5, HEK293 and A549 cells. NFκB p65 expression level was very low in NFκB Δp65⁻ A549 cells whereas it has high expression in DMA+Radiation condition in scramble A549 cell line (FIG. 10C). Subsequently the expression level of IκBα was lower in DMA+Radiation condition and pIKKα/β were elevated in DMA+Radiation condition in both the cell lines (FIG. 10C). PTEN level was almost constant in all conditions in both cell lines which was concurrent with previous results in cell lines (FIG. 10C). As DMA itself is a DNA minor groove binder molecule, we observed upregulation of NFκB in both DMA alone and in combination with radiation due to synergistic effect of molecule itself along with activation of Akt/NFκB pathway. All these results indicate that DMA has modulatory effect on Akt/NFκB pathway which acts through interrelated cascade of reactions involved in cell cycle, DNA repair, apoptosis and cell survival at the transcriptional level to render radioprotection in Balb/c mice (FIG. 10D).

The most optimized methodology for the present invention is explained in the form of examples below. The present invention is, however, not limited to these examples in any manner. The following examples are intended to illustrate the working of disclosure and not intended to take restrictively to apply any limitations on the scope of the present invention. Those persons skilled in the art will understand that the equivalent substitutes to the specific substances described herein, or the corresponding improvements in the process are considered to be within the scope of this invention.

DETAILED METHODOLOGY AND EXPERIMENTAL DATA AND RESULTS

Example 1

Study Design

Animal studies were conducted according to guidelines of Committee for the purpose of control and supervision of experiments on animals (CPCSEA), Government of India and reported as per the ARRIVE (Animal Research: Reporting In Vivo experiments) guidelines. Randomization of animals onto study was based on initial tumor volumes to ensure equal distribution across groups. A power analysis was performed to calculate group sizes to enable statistically robust detection of survival of animal in response to DMA against lethal TBI (10/group), tumor growth inhibition (5 per group) or Pharmacokinetics and biodistribution endpoint (3/group).

Example 2

In Vitro Cell Culture

The Human Embryonic Kidney cell line (HEK293), human lung fibroblast (MRC-5), Human glioblastoma (U87) and human lung adenocarcinoma epithelial (A-549) cell lines were grown until; 80% confluent trypsinized and seeded in 90-mm petri dish 24 h before the experiment. Four groups, control (untreated), DMA treated, radiation, and DMA+radiation-treated were studied in all three cell lines.

Example 3

Cytotoxicity Assay

Exponentially growing HEK293, MRC5 and A549 cells were plated at cell densities 3000 cells per well in 96-well tissue culture plates. At 24, 48 and 72 h, cells were treated with increasing concentrations of DMA i.e.; 0.1-100 µM. Cytotoxicity was measured by MTT assay according to the manufacturer's instructions (Promega, Madison, Wis., USA).

Uptake and Efflux Study of DMA in HEK293 Cells

HEK293 cells ($10^6$ cells/ml) were seeded overnight and incubated at 37° C. in a complete medium. Cells were treated with prewarmed complete media to 37° C. containing DMA at 501 µM concentration for 2 h. After incubation time, cells were collected by centrifugation, resuspended in cold (4° C.) phosphate-buffered saline and placed on ice for subsequent flow cytometry analysis.

Clonogenicity of DMA in U87, HEK293, MRC5 and A549 Cells

Exponentially growing U87, HEK293, MRC5 and A549 cells were treated with 50 µM DMA for 2 h and irradiated with 0, 1, 2, 5, 8 and 10 Gy of radiation dose as indicated at RT and trypsinized immediately at 37° C. Cells were seeded into 60 mm dishes in triplicate at various cell densities aiming approximately 100 colonies/dish. Percentage radioprotection was calculated by following formula % of Protection in radiation treated cells=
$(SF_{DMA+radiaion})-(SF_{Radiaion})/SF_{Control} \times 100$ Where SF is survival fraction in respective conditions. Dose modification factor (DMF) was calculated as ratio of 50% survival in DMA+radiation to 50% survival in radiation only.

Example 4

In Vivo Experiments

DMA and IR Exposure Conditions 2 h subsequent to DMA treatment, cells was exposed to γ-irradiation (1.3 Gy/min dose rate) using Co-60 source (Institute of Nuclear Medicine and Allied Sciences, Delhi, India). Following irradiation, cells were incubated for 4 h in a 5% $CO_2$ humidified incubator and processed for further sample preparation.

Balb/c mice with or without DMA treatment were placed in a specially designed, well-ventilated acrylic container and subjected to whole-body irradiation at 5, 6, 8, 9 or 10 Gray (Gy) in a single fraction.

In Vivo Anti-Tumor Activity Against Ehrlich Ascites Tumor (EAT) and Melanoma Tumor EAT and Melanoma Tumor Model:

EAT and B16F10 melanoma cell line were harvested and $10 \times 10^6$ and $0.8 \times 10^6$ cells respectively were injected subcutaneously in the Balb/c mice (n=24) on the right thigh. When tumors reached 0.5 $cm^3$ in volume, animals were randomized and divided into 4 different groups. The first test group was treated with 50 mg/kg, i.v. DMA, second test group subjected to 8 Gy TBI. Third group received 50 mg/kg, i.v. DMA and 8 Gy TBI both. The control group was similarly administered normal saline (0.1 ml, i.v.). On every alternate days, tumor-bearing thigh of each animal was shaved, and the longest (1) and shortest diameter (b) of the tumors along with height (h) were measured with the help of a vernier calliper. Tumor weight of each animal was calculated using the formula l*b*h/2. Animals were observed for 30 days for their body weight, food and water intake, signs of radiation sickness and mortality.

Tissue Histopathology

The hepatic, spleen and small intestine specimens were collected from Balb/c mice and tumor bearing mice three days after 8 Gy TBI with or without pre-treatment with DMA (50 mg/kg) 2 hour before TBI. Tissue specimens were fixed in 10% buffered formalin, embedded in paraffin, sectioned and stained with H&E and examined using an upright trinocular microscope attached to a CCD camera.

Example 5

Determination of Effective Radioprotective Dose of DMA

The mice were grouped as follows: Group 1, Sham control (normal saline treated); Group 2, radiation control (whole body exposure to 8 Gy); Group 3, treated with increasing doses (100, 150, 200, 450 and 600 mg/kg bw) of DMA 2 h prior to whole body exposure to 8 Gy and Group 4 treated with similar DMA doses only. Survival study was carried out for a period of 30 days and animals were routinely monitored for their body weight, food and water intake, radiation sickness symptoms and mortality to fix the highest effective dose of DMA against radiation induced toxicity.

Dose Reduction Factor Analysis (DRF)

Mice were treated with DMA (200 mg/kg bw) prior to whole body exposure to 5, 6, 8, 9 & 10 Gy. DRF was calculated ratio of LD50/30 mice treated with both DMA and radiation to the LD50/30 of mice treated with saline and radiation. Similarly survival with different route of administration of DMA was studied at 8 and 9 Gy TBI.

Nude Mice Survival

Mice were divided into 4 groups containing 5 animals each. Group 1, sham control; Group 2, DMA treated (50 mg/kg, i.p.); Group 3, TBI 7Gy; Group 4, treated with DMA (50 mg/kg i.p.) prior to TBI 7Gy. Animals were observed for 30 days for their body weight, food and water intake, signs of radiation sickness and mortality.

Example 6

Assessment of Cells Viability by BrdU Labelling in the Spleen and IL6 Labeling in Small Intestine Spleen cell survival was determined 3 days after irradiation by 5-bromo-2'-deoxyuridine (BrdU, i.p., 100 mg/kg) to each mouse 2 h before euthanasia. Similarly small intestine was checked for IL6 expression. BrdU and IL6 immunohistochemistry (IHC) were performed as per standard protocol against BrdU and IL6. 3,3,-diaminobenzidine (DAB) was used to detect antigen-antibody binding. Counterstaining was done with hematoxylin, and after dehydration, slides were mounted with glycerogelatin.

Example 7

Assessment of the Cell Proliferation by BrdU Labeling

S phase cells were labeled in vivo by administering BrdU (i.p., 100 mg/kg) to each mouse 2 h before euthanasia. Mice were euthanized 3 days after irradiation and small intestine was rapidly dissected, chopped into homogeneous solution by straining with 70μ strainer and fixed in 70% ethanol. Cells stained with 0.5 mL of RNase (2 mg/mL) and 0.5 mL of propidium iodide (0.1% in 0.6% Triton X-100 in PBS) for 30 min in dark. Samples were then analysed on a FACS Calibur flow-cytometer (Becton Dickinson).

Example 8

Endogenous Spleen Colony Forming Assay

Group 1, sham control (normal saline treated); Group 2, DMA treated (200 mg/kg bw); Group 3, radiation control (whole body exposure to 8Gy); Group 4, treated with DMA (200 mg/kg bw) prior to whole body exposure to 8Gy. Mice (6 animals each) were irradiated, 2 h post-administration of DMA. The mice were sacrificed on day 10 and spleens were removed, blotted free of blood, weighed and the spleen index was calculated [spleen index=(spleen weight/body weight)×100]. Subsequently spleens were fixed in Bouin's fixative for 15 min and the number of macroscopic spleen cell colonies was counted manually.

Example 10

Biochemical Estimations for Antioxidant Enzymes and Total Protein in Liver

Mice hepatic tissues were homogenised using REMI homogenizer in phosphate buffer and centrifuged at 10,000×g for 15 min and aliquots of supernatant were separated. The supernatant was used for the biochemical estimations using standard spectrophotometric reported methods. The total protein was determined by the Lowry method.

Example 11

Total Thiols Estimation, Lipid Peroxidation

The liver supernatant was incubated for 10 min and the absorbance was measured at 412 nm and total thiol content was calculated by standard method. The amount of MDA was done by reaction with thiobarbituric acid (TBA) at 532 nm by literature method.

Example 12

Estimation of Reduced Glutathione

Glutathione was measured according to the Ellman's method.

Example 13

Superoxide Dismutase (SOD), Glutathione-S-Transferase (GST) and Glutathione Reductase (GR) Activity Superoxide dismutase (SOD) activity was assayed according to the Marklund and Marklund method. The activity of GST was determined by using CDNB as the substrate. The reaction mixture contained 1 mM of CDNB, 1 mM GSH in 0.1M phosphate buffer (pH 6.5). The formation of the GSH-CDNB conjugate was determined at 340 nm and the activity was calculated by using e=9.6 mM-1 cm-1.

Example 14

Immunoblot Analysis

HEK293, MRC5 and A549 cells were treated as indicated earlier. The cell pellet was resuspended in RIPA buffer and allowed to swell on ice for 30 min. Balb/c intestine tissue and tumor tissues were homogenized in RIPA buffer. Protein concentration was determined using Bradford's Assay (Bangalore Genei). Western blot was performed using standard protocols with primary antibodies against Akt, pAkt (Ser-473), GSK33, pGSK33, mTOR, p70, Bad, PTEN, IKKα/β, p IKKα/β, p53, Bcl2, GAPDH, and NFκB (p65) (Cell Signalling) and horseradish peroxidase-conjugated mouse or rabbit secondary antibody (Abcam). Signals were detected using enhanced chemiluminescence (ECL system, Pierce) on X-ray film.

Example 15

Akt Kinase Assay

Akt kinase activity was determined using Akt Kinase Assay Kit (Nonradioactive) (Cell Signaling Technology, Cat. #9840) following the manufacturer's instructions.

Example 16

In Vivo Pharmacokinetics and Bio-Distribution of DMA

Blood Sampling and Plasma Extraction:

Oral and intravenous pharmacokinetics of DMA was performed at a dose of 100 and 50 mg/kg bw, respectively. Control mice were administered equal volume of sterile water. Blood samples were collected by cardiac puncture at 1, 2, 4, 6, 16, and 24 h after oral and intravenous administration of DMA. Plasma was spiked with Hoechst 33342 as internal standard. Plasma proteins were precipitated by adding 180 μl acetonitrile and the samples were centrifuged at 14000 rpm for 10 min at 4° C. Clear supernatant (20001) was taken and 2001 distilled water was added to get a ~35% acetonitrile solution. The samples were injected onto HPLC-MS/MS system.

Tissue Samples Preparation:

Tissue samples were collected from the same mice from which blood samples were collected in both doses of DMA. Lung, liver, kidney, intestine, heart, spleen, brain were dissected and rinsed with phosphate buffer saline (PBS) and dried on blotting paper. 100 mg of tissue sample was homogenized for 20 s in chilled acetonitrile and water and further 700 µl chilled acetonitrile was added. The sample was centrifuged at 14000 rpm for 10 min and clear supernatant was collected for analysis on HPLC-MS/MS system.

Example 17

Bioanalysis

A standard DMA calibration from 1-1000 ng/ml with internal standard (20 ng/ml) was quantified. Sample analysis was performed on positive ionization mode LC-MS/MS with multiple reactions monitoring (MRM, m/z Q1/Q3) of DMA (m/z 235.1/412.0, retention time (RT) 5.3 min) and internal standard (m/z 227.1/396.0, RT 6.5 min) (Agilent 6410 series). A gradient method was employed to analyze the plasma samples using mobile phase A (0.1% formic acid in water) and mobile phase B (methanol). The B % was set as 30 (0 min), 90 (10-14 min), 30 (14-24 min) with flow rate of 0.3 ml/min. An injection volume of 10 µl was used for analysis.

Example 18

Pharmacokinetics and Bio-Distribution Analysis

Peak tissue concentration ($C_{max}$) of DMA and time to reach the $C_{max}$ ($t_{max}$) were read directly from the raw data by visual examination of mean tissue concentration-time profile. The tissue concentration-time data following oral dose were subjected to one-, two- and three-compartmental models using WinNonlin program (version 6.3; Certara Inc, Missouri, USA) to calculate the pharmacokinetic parameters. The pharmacokinetic models were compared according to maximal correlation between observed and predicted concentration, minimal sum of squared residuals, Akaike Information Criterion (AIC) and Schwarz Bayesian Criterion (SBC). However, the tissue concentration-time data following intravenous administration were subjected to non-compartmental approach.

Example 19

Gene Expression Analysis at mRNA Level by RT-PCR

The cDNA generated from total RNA was amplified using 1 µl of the reaction products in 10 µl with respective primers for 45 cycles following standard RT-PCR cycle by SYBR green dye. Transcript levels were calculated according to the $2^{-\Delta\Delta Ct}$ method, normalized to the expression of GAPDH, and expressed as fold change compared with control.

Example 20

Proliferation Kinetics in Presence of Inhibitors

HEK293 cells post 50 µM LY294002 (PI3K/Akt inhibitor) and 10 µM PS1145 (NFκB inhibitor) treatment were treated with 50 µM DMA and 5 Gy radiation. Same experiment was done with control (no inhibitor), only LY294002 and only PS1145 treated HEK cells. Percentage (%) radioprotection of cells at 24, 48 and 72 h was calculated by following formula—

% growth of Radiation treated cells=($CN_{Radiation}$/$CN_{Control}$)×100.

% growth of DMA+Radiation treated cells=($CN_{DMA+Radiation}$/$CN_{Control}$)×100.

% Radioprotection=% growth of DMA+Radiation treated cells−% growth of Radiation treated cells where CN is the cell number.

Example 21

Extraction of Cytosolic and Nuclear Proteins

Cytosolic Protein Extraction:

Cells after treatment were collected by trypsinization and washed twice with ice-cold PBS. Cell pellet was resuspended in five volumes of cytoplasmic extraction buffer (CEB) [10 mM HEPES pH 7.9, 10 mM KCl, 0.1 mM EDTA, 0.3% NP-40 and 1× protease inhibitor cocktail] to the size of cell pellet for 5 min. Protein solution was centrifuged at 3000 rpm for 5 min at 4° C. and supernatant was harvested as cytoplasmic extract.

Nuclear Protein Extraction:

The cell pellet obtained after extraction of cytoplasmic proteins was resuspended again in CEB without NP-40. It was centrifuged at 3000 rpm for 5 min at 4° C. and supernatant was discarded. Equal volume of nuclear extraction buffer (NEB) [20 mM HEPES pH7.9, 0.4M NaCl, 1 mM EDTA, 25% Glycerol, and 1× protease inhibitor cocktail] was added to nuclear pellet and incubated on ice for 10 min. Supernatant was harvested as nuclear protein extract.

Example 22

Knockdown of Akt Gene Expression Using siRNA

HEK 293 cells were transfected with Akt siRNA and control-siRNA (Santa Cruz Biotechnology Inc.) according to the manufacturer's instructions. Semi-quantitative RT-PCR was performed with primers specific for Akt and ACTB in control siRNA and Akt siRNA treated HEK cells for analysing knockdown of Akt and ACTB gene expression.

Example 23

Cell-Cycle Analysis

The cell cycle analysis of Akt depleted HEK293 cells were done at 0, 1, 3, 6, 12, 18 and 24 h, washed twice with ice-cold PBS, and fixed in 70% ethanol. Cell pellets were stored at 4° C. for 24 h, and stained with 0.5 mL of propidium iodide (0.1% in 0.6% Triton X-100 in PBS) and 0.5 mL of RNase (2 mg/mL) for 30 min in dark. Samples were then analysed on a FACS Calibur flow-cytometer (Becton Dickinson).

Example 24

Annexin-V Staining

HEK293 cells (2×10$^5$ cells/plate) were transfected with control siRNA and siRNA-Akt, and DMA, Radiation and DMA+Radiation treatments were given as described earlier and samples were collected at 3, 6, 12, 18 and 24 h (data not shown for 12 and 18 h). Samples were prepared according to the manufacturer's instructions (BD Pharmingen™ Annexin V: FITC Apoptosis Detection Kit I, Catalog Number 556547, USA) and the samples were subjected to flow cytometry analysis (Becton Dickinson).

Example 25

Clonogenicity Assay with Akt Depleted Cells

Exponentially growing HEK cells post siRNA (siRNA-Akt and control siRNA transfections) were treated with 50 µM DMA for 1 h and irradiated with 0, 1, 2, 5 and 8 Gy of radiation dose at RT. Cells were seeded into 60 mm dishes in triplicate, at various densities and cells were stained with crystal violet to count colonies. Same experiment was done with control siRNA-transfected HEK cells. Percentage radioprotection was calculated by following formula % of Protection in radiation treated cells=(Survival fraction in siRNA+DMA treated cells/Survival fraction in only siRNA treated cells/)×100.

Example 25

Generation of NFκB p65 Knockdown (Δp65⁻) A549 Cells
NFκB p65 shRNA Cloning in pLKO TRC1 Vector:
Annealed oligo sequences NFκB FP 5'-CCGGCACCAT-CAACTATGATGAGTTCTCGAGAACTCATCATAGTT-GAT GGTGTTTTTG-3'; NFκB RP 5'-AAT-TCAAAAACACCATCAACTATGATGAGTTCTCGAGA ACTCATCATAGTTGATGGTG-3' was cloned in pLKO TRC1 vector.

Lentivirus Production of NFκB p65 shRNA Clone in 10 cm Plate:
Mix of Lipofectamine (Invitrogen, India), (pCMV-R8.74psPAX2), envelope plasmid (pMD2.G), NFκB p65 shRNA cloned plasmid and OPTI-MEM (Invitrogen, India) were incubated at room temperature for 30 min. Cells were transfected with this transfection mix After 24 h incubation media was harvested containing lentivirus, replenished with fresh new high serum media and further harvested lentivirus. Lentiviruses were stored in −80° C. for long term storage. Similarly lentiviruses with scrambled shRNA clone were harvested.

Lentiviral Infection and Selection of NFκB p65 Knockdown A549 Cells:
0.8-1×10⁶ A549 cells were seeded with media containing 8 μg/ml polybrene. Cells were infected with 0.5 ml lentivirus in fresh media containing polybrene and were incubated for next 24 h. Desired cells were selected against puromycin. NFκB p65 protein knockdown was checked by western blot after 3 days of selection media.

Example 26

Clonogenicity Assay of NFκB p65 Knockdown (Δp65⁻) A549 Cells with DMA
Exponentially growing scrambled and NFκB p65 knockdown A549 cells were treated with 50 μM DMA for 2 h and irradiated with 0, 2, 4, 6 and 8 Gy of radiation dose for clonogenic survival assay. % Radioprotection was calculated by following formula % of Protection in radiation treated cells=(SF$_{(\Delta p65-)+DMA}$/SF$_{(\Delta p65-)}$)×100 where SF is survival fraction in respective conditions.

Example 27

Statistical Analysis
Experiments were performed in triplicate and the results are presented as means±SD. Statistical significance among groups was determined using the Student's t test and the one-way ANOVA followed by Tukey's Multiple Comparison as posthoc test for in vivo results using Graph Pad Prism software (version 5.0) software to confirm the variability of data and validity of results. P<0.05 was considered statistically significant data. Log-rank test was performed to determine significance in animal survival study.

SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. A method of protecting
    a. non-cancerous mammalian cells or
    b. normal cells or tissues in a mouse with (i) melanoma or (ii) an Ehrlich ascites tumor
    from radiation damage, comprising administering an effective amount of (5-(4-methylpiperazin-1-yl)-2-[2'-(3,4-dimethoxyphenyl)-5'-benzimidazolyl]benzimidazole (DMA) to the mammalian cells or to the mouse before exposing the cells or the mouse to radiation.
2. The method of embodiment 1, wherein the radiation is radiation therapy.
3. The method of embodiment 1 or embodiment 2, which comprises administering DMA to a mouse with (i) melanoma or (ii) an Ehrlich ascites tumor and then exposing the mouse to total body irradiation.
4. The method of embodiment 3, wherein the administration of DMA selectively protects normal cells or tissues over tumor cells or tissues against lethal total body irradiation.
5. The method of any one of embodiments 1 to 4, which comprises administering DMA to the mouse and wherein the administration of DMA results in increased survival of the tumor bearing mouse compared to a tumor bearing mouse to not administered DMA and exposed to the same dose of radiation.
6. The method of any one of embodiments 1 to 5, wherein the administration of DMA does not activate Akt/NFκB pathway in tumor cells or tissues against radiation.
7. The method of any one of embodiments 1 to 6, wherein the administration of DMA maintains antioxidant enzymes, ameliorates radiation induced hematopoietic (HP) and gastrointestinal (GI) system damage and modulation of genes when administered prior to total body irradiation.
8. The method of embodiment 7, wherein the administration of DMA reverses HP and GI damage caused by radiation.
9. The method of any one of embodiments 1 to 8, wherein the administration of DMA regulates cellular antioxidant level and modulatory effect on mRNA expression.
10. The method of embodiment 9, wherein the administration of DMA regulates cell proliferation and apoptosis related genes in the intestine without altering cell cycle and regulates Akt/NFκB signalling transduction pathway to render radioprotection in normal cells or tissues.
11. The method of any one of embodiments 1 to 10, wherein the administration of DMA does not protect tumor cells or tissues against total body irradiation.
12. The method of any one of embodiments 1 to 11, wherein the administration of DMA also regulates radiation induced redox balance.
13. The method of any one of embodiments 1 to 12, wherein the DMA is administered orally or intravenously.
14. The method of embodiment 13, wherein a single 200 mg/kg oral or 50 mg/kg intravenous (i.v.) dose of DMA is administered.
15. The method of embodiment 14, wherein the single dose augments 80 and 100% survival at 8Gy.
16. The method of any one of embodiments 13 to 15, wherein the DMA is rapidly cleared from plasma following administration.

17. The method of any one of embodiments 1 to 16, wherein protection of mammalian cells or normal cell or tissues is hindered by the knockdown of Akt and NFκB p65.

18. The method of any one of embodiments 1 to 17, wherein the mouse is a nude mouse.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

REFERENCES

Nair, C. K., D. K. Parida, and T. Nomura. 2001. Radioprotectors in radiotherapy. *J Radiat Res* 42:21-37.

Begg, A. C., F. A. Stewart, and C. Vens. 2011. Strategies to improve radiotherapy with targeted drugs. *Nature reviews. Cancer* 11:239-253.

Brizel, D. M., T. H. Wasserman, M. Henke, V. Strnad, V. Rudat, A. Monnier, F. Eschwege, J. Zhang, L. Russell, W. Oster, and R. Sauer. 2000. Phase III randomized trial of amifostine as a radioprotector in head and neck cancer. *Journal of clinical oncology: official journal of the American Society of Clinical Oncology* 18:3339-3345.

Burdelya, L. G., V. I. Krivokrysenko, T. C. Tallant, E. Strom, A. S. Gleiberman, D. Gupta, O. V. Kurnasov, F. L. Fort, A. L. Osterman, J. A. Didonato, E. Feinstein, and A. V. Gudkov. 2008. An agonist of toll-like receptor 5 has radioprotective activity in mouse and primate models. *Science (New York, N.Y.)* 320:226-230.

Kalpana, K. B., N. Devipriya, M. Srinivasan, P. Vishwanathan, K. Thayalan, and V. P. Menon. 2011. Evaluating the radioprotective effect of hesperidin in the liver of Swiss albino mice. *European journal of pharmacology* 658:206-212.

Kamran, M. Z., A. Ranjan, N. Kaur, S. Sur, and V. Tandon. 2016. Radioprotective Agents: Strategies and Translational Advances. *Medicinal research reviews*.

Kaur, N., A. Ranjan, V. Tiwari, R. Aneja, and V. Tandon. 2012. DMA, a bisbenzimidazole, offers radioprotection by promoting NFkappaB transactivation through NIK/IKK in human glioma cells. *PloS one* 7:e39426.

Nair, C. K., D. K. Parida, and T. Nomura. 2001. Radioprotectors in radiotherapy. *Journal of radiation research* 42:21-37.

Nimesh, H., V. Tiwari, C. Yang, S. R. Gundala, K. Chuttani, P. P. Hazari, A. K. Mishra, A. Sharma, J. Lal, A. Katyal, R. Aneja, and V. Tandon. 2015. Preclinical Evaluation of DMA, a Bisbenzimidazole, as Radioprotector: Toxicity, Pharmacokinetics, and Biodistribution Studies in Balb/c Mice. *Molecular pharmacology* 88:768-778.

Prabhakar, K. R., V. P. Veerapur, P. Bansal, V. K. Parihar, M. Reddy Kandadi, P. Bhagath Kumar, K. I. Priyadarsini, and M. K. Unnikrishnan. 2007. Antioxidant and radioprotective effect of the active fraction of *Pilea microphylla* (L.) ethanolic extract. *Chemico-biological interactions* 165:22-32.

Ranjan, A., N. Kaur, V. Tiwari, Y. Singh, M. M. Chaturvedi, and V. Tandon. 2013. 3,4-Dimethoxyphenyl bis-benzimidazole derivative, mitigates radiation-induced DNA damage. *Radiation research* 179:647-662.

Singh, M., and V. Tandon. 2011. Synthesis and biological activity of novel inhibitors of topoisomerase I: 2-aryl-substituted 2-bis-1H-benzimidazoles. *European journal of medicinal chemistry* 46:659-669.

Singh, S. P., V. R. Jayanth, S. Chandna, B. S. Dwarakanath, S. Singh, J. S. Adhikari, and V. Jain. 1998. Radioprotective effects of DNA ligands Hoechst-33342 and 33258 in whole body irradiated mice. *Indian journal of experimental biology* 36:375-384.

Tawar, U., S. Bansal, S. Shrimal, M. Singh, and V. Tandon. 2007. Nuclear condensation and free radical scavenging: a dual mechanism of bisbenzimidazoles to modulate radiation damage to DNA. *Molecular and cellular biochemistry* 305:221-233.

Tawar, U., A. K. Jain, B. S. Dwarakanath, R. Chandra, Y. Singh, N. K. Chaudhury, D. Khaitan, and V. Tandon. 2003. Influence of phenyl ring disubstitution on bisbenzimidazole and terbenzimidazole cytotoxicity: synthesis and biological evaluation as radioprotectors. *Journal of medicinal chemistry* 46:3785-3792.

Wang, H., Y. Jia, P. Gao, Y. Cheng, M. Cheng, C. Lu, S. Zhou, and X. Sun. 2013. Synthesis, radioprotective activity and pharmacokinetics characteristic of a new stable nitronyl nitroxyl radical-NIT2011. *Biochimie* 95:1574-1581.

Young, S. D., and R. P. Hill. 1989. Radiation sensitivity of tumour cells stained in vitro or in vivo with the bisbenzimide fluorochrome Hoechst 33342. *British journal of cancer* 60:715-721.

We claim:

1. An in vivo method of protecting normal cells or tissues in a mouse with (i) melanoma or (ii) an Ehrlich ascites tumor from radiation damage comprising administering orally or intravenously an effective amount of (5-(4-methylpiperazin-1-yl)-2-[2'-(3,4-dimethoxyphenyl)-5'-benzimidazolyl]benzimidazole (DMA) to the mouse before exposing the mouse to radiation, wherein the administration of DMA selectively protects normal cells or tissues from radiation damage over tumor cells or tissues.

2. The method of claim 1, which comprises administering DMA to a mouse with (i) melanoma or (ii) an Ehrlich ascites tumor and then exposing the mouse to total body irradiation.

3. The method of claim 2, wherein the administration of DMA selectively protects normal cells or tissues over tumor cells or tissues against lethal total body irradiation.

4. The method of claim 2, which comprises administering DMA to the mouse and wherein the administration of DMA results in increased survival of tumor bearing mouse compared to an irradiated tumor bearing mouse not administered DMA.

5. The method of claim 1, wherein the administration of DMA does not activate Akt/NFκB pathway in tumor tissues against radiation.

6. The method of claim 2, wherein the administration of DMA maintains antioxidant enzymes, ameliorates radiation induced hematopoietic (HP) and gastrointestinal (GI) system damage and modulation of genes when administered prior to total body irradiation.

7. The method of claim 6, wherein the administration of DMA reverses HP and GI damage.

8. The method of claim 1, wherein the administration of DMA regulates cellular antioxidant level and modulatory effect on mRNA expression.

9. The method of claim 8, wherein the administration of DMA regulates cell proliferation and apoptosis related genes in the intestine of the mouse without altering cell cycle and regulates Akt/NFκB signalling transduction pathway to render radioprotection in normal cells or tissues.

10. The method of claim 1, wherein the administration of DMA does not protect the tumor against total body irradiation.

11. The method of claim 1, wherein the administration of DMA also regulates radiation induced redox balance.

12. The method of claim 1, wherein a single 200 mg/kg oral and 50 mg/kg intravenous (i.v.) DMA dose augments 80 and 100% survival at 8Gy, respectively.

13. The method of claim 1, wherein the DMA is rapidly cleared from plasma following administration.

14. The method of claim 1, wherein protection of mammalian cells or normal cells or tissues is hindered by the knockdown of Akt and NFκB p65.

15. The method of claim 1, wherein the mouse is a nude mouse.

16. The method of claim 1, wherein the radiation is radiation therapy.

* * * * *